United States Patent
Lawrence et al.

(10) Patent No.: US 12,390,427 B2
(45) Date of Patent: Aug. 19, 2025

(54) PLASMINOGEN ACTIVATOR INHIBITOR-1 (PAI-1) INHIBITOR AND METHOD OF USE

(71) Applicants: REGENTS OF THE UNIVERSITY OF MICHIGAN, Ann Arbor, MI (US); EASTERN MICHIGAN UNIVERSITY, Ypsilanti, MI (US)

(72) Inventors: Daniel A. Lawrence, Ann Arbor, MI (US); Cory Emal, Ann Arbor, MI (US); Ashley Reinke, Appleton, WI (US); Shih-Hon Li, Canton, MI (US)

(73) Assignees: EASTERN MICHIGAN UNIVERSITY, Ypsilanti, MI (US); THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 17/883,245

(22) Filed: Aug. 8, 2022

(65) Prior Publication Data

US 2022/0387356 A1 Dec. 8, 2022

Related U.S. Application Data

(62) Division of application No. 16/631,066, filed as application No. PCT/US2018/043998 on Jul. 27, 2018, now Pat. No. 11,426,368.

(60) Provisional application No. 62/537,513, filed on Jul. 27, 2017.

(51) Int. Cl.
*C07C 243/32* (2006.01)
*A61K 31/137* (2006.01)
*C07C 243/26* (2006.01)

(52) U.S. Cl.
CPC .................................. *A61K 31/137* (2013.01)

(58) Field of Classification Search
CPC ... C07C 243/26; C07C 243/32; A61K 31/137; A61K 31/15
See application file for complete search history.

(56) References Cited

U.S. PATENT DOCUMENTS

| | | |
|---|---|---|
| 4,618,692 A | 10/1986 | Scheffler et al. |
| 4,801,749 A | 1/1989 | Kazmierczak et al. |
| 6,528,655 B1 | 3/2003 | N'Zemba et al. |
| 7,351,730 B2 | 4/2008 | Mayer et al. |
| 8,759,327 B2 | 6/2014 | Lawrence et al. |
| 9,120,744 B2 | 9/2015 | Lawrence et al. |
| 9,718,760 B2 | 8/2017 | Lawrence et al. |
| 10,626,112 B2 | 4/2020 | Kobayashi et al. |
| 10,723,785 B2 | 7/2020 | Eckelman et al. |
| 11,426,368 B2 | 8/2022 | Lawrence et al. |
| 2002/0052513 A1 | 5/2002 | Broadhurst et al. |
| 2005/0124664 A1 | 6/2005 | Sartori et al. |
| 2006/0058243 A1 | 3/2006 | Chen et al. |
| 2007/0155747 A1 | 7/2007 | Dasse et al. |
| 2010/0137194 A1 | 6/2010 | Lawrence et al. |
| 2015/0315178 A1 | 11/2015 | Lawrence et al. |

FOREIGN PATENT DOCUMENTS

| | | |
|---|---|---|
| CN | 101351495 A | 1/2009 |
| EP | 0555893 A1 | 8/1993 |
| EP | 1124157 A2 | 8/2001 |
| EP | 1719763 A1 | 11/2006 |
| JP | 1989-066154 A | 3/1989 |
| JP | 1998-287622 A | 10/1998 |
| JP | 2000171937 A | 6/2000 |
| JP | 2014523900 A | 9/2014 |
| JP | 7291119 B2 | 6/2023 |
| WO | WO-92/00968 A1 | 1/1992 |
| WO | WO-94/29267 A1 | 12/1994 |
| WO | WO-99/42435 A2 | 8/1999 |
| WO | WO-03/055843 A1 | 7/2003 |
| WO | WO-2005/000330 A1 | 1/2005 |
| WO | WO-2007/127505 A2 | 11/2007 |
| WO | WO-2009/017848 A1 | 2/2009 |
| WO | WO-2014/070983 A1 | 5/2014 |
| WO | WO-2015115507 A1 | 8/2015 |
| WO | WO-2019023526 A1 | 1/2019 |

OTHER PUBLICATIONS

Izuhara et al. Arteriosclerosis, Thrombosis and Vascular Biology 2008, 28 (4), 672-677.*
Fortenberry Expert Opinion of Therapeutic Patents 2013, 23 (7), 801-815.*
Ghosh et al. Journal of Cellular Physiology 2012, 227, 493-507.*
Alessi et al., Production of plasminogen activator inhibitor 1 by human adipose tissue: possible link between visceral fat accumulation and vascular disease. Diabetes. 46: 860-7 (1997).
Ashton et al., Nonpeptide angiotensin II antagonists derived from 4H-1,2,4-triazoles and 3H-imidazo[1,2-b][1,2,4] triazoles, J. Med. Chem., 36(5):591-609 (1993).
Berkenpas et al., Molecular evolution of plasminogen activator inhibitor-1 functional stability. EMBO J. 14: 2969-77 (1995).
Biemond, Thrombolysis and reocclusion in experimental jugular vein and coronary artery thrombosis. Effects of a plasminogen activator inhibitor type 1-neutralizing monoclonal antibody. Circulation. 91: 1175 (1995).

(Continued)

*Primary Examiner* — Irina Neagu

(74) *Attorney, Agent, or Firm* — MARSHALL, GERSTEIN & BORUN LLP

(57) ABSTRACT

Provided herein are plasminogen activator-1 (PAI-1) inhibitor compounds and uses thereof in the treatment of any disease or disorder associated with elevated PAI-1. The disclosure includes, but is not limited to, the use of such compounds to prevent or reduce thrombosis and fibrosis, to promote thrombolysis, and to modulate lipid metabolism and treat diseases or disorders associated with elevated PAI-1, cholesterol, or lipid levels.

4 Claims, 9 Drawing Sheets

(56) References Cited

OTHER PUBLICATIONS

Boncoraglio et al., An effect of the PAI-1 4G/5G polymorphism on cholesterol levels may explain conflicting associatations with myocardial infarction and stroke. *Cerebrovascular Dis.* 22(2-3): 191-5 (2006).
Booth, Fibrinolysis and thrombosis. Baillieres Best. Pract. Res. Clin. Haematol. 12: 423-33 (1999).
Boucher et al., LRP: role in vascular wall integrity and protection from atherosclerosis. Science. 300: 329-32 (2003).
Bu, Receptor-associated protein: a specialized chaperone and antagonist for members of the LDL receptor gene family. Curr. Opin. Lipidol. 9: 149-55 (1998).
Butenas et al., Ultrasensitive fluorogenic substrates for serine proteases. Thromb. Haemost. 78: 1193-1201 (1997).
Cao et al., A specific role of integrin Mac-1 in accelerated macrophage efflux to the lymphatics. Blood. 106: 3234-41 (2005).
Cao et al., Endocytic receptor LRP together with tPA and PAI-1 coordinates Mac-1-dependent macrophage migration. EMBO J. 25: 1860-70 (2006).
Chen et al., 4G/5G promoter polymorphism of plasminogen activator inhibitor-1, lipid profiles, and ischemic stroke. *J. Lab. Clin. Med.* 142(2): 100-5 (2003).
Chmielewska et al., Evidence for a rapid inhibitor to tissue plasminogen activator in plasma. Thromb. Res. 31: 427-36 (1983).
Choi et al., Generation of oxamic acid libraries: antimalarials and inhibitors of Plasmodium falciparum lactate dehydrogenase, J. Comb. Chem., 9(2):292-300 (2007).
Cigolini et al., Expression of plasminogen activator inhibitor-1 in human adipose tissue: a role for TNF-alpha? Atherosclerosis. 143: 81-90 (1999).
Clausen et al., Conditional gene targeting in macrophages and granulocytes using LysMcre mice. Transgenic Res. 8: 265-77 (1999).
Colucci et al., Generation in plasma of a fast-acting inhibitor of plasminogen activator in response to endotoxin stimulation. J. Clin. Invest. 75: 818-24 (1985).
Crandall et al., Characterization and comparative evaluation of a structurally unique PAI-1 inhibitor exhibiting oral in-vivo efficacy. J. Thromb. Haemost. 2: 1422-1428 (2004).
Crandall et al., Modulation of adipose tissue development by pharmacological inhibition of PAI-1. Arterioscler. Thromb. Vasc. Biol. 26: 2209-15 (2006).
Crandall et al., Release of PAI-1 by human preadipocytes and adipocytes independent of insulin and IGF-1. Biochem. Biophys. Res. Commun. 279: 984-8 (2000).
Cuchel et al., Macrophage reverse cholesterol transport: key to the regression of atherosclerosis? Circulation. 113: 2548-55 (2006).
Czekay et al., Plasminogen activator inhibitor-1 detaches cells from extracellular matrices by inactivating integrins. J. Cell. Biol. 160: 781-91 (2003).
Daci et al., Mice lacking the plasminogen activator inhibitor 1 are protected from trabecular bone loss induced by estrogen deficiency. J. Bone Miner. Res. 15: 1510-6. (2000).
De Taeye et al., Bone marrow plasminogen activator inhibitor-1 influences the development of obesity. J. Biol. Chem. 281: 32796-805 (2006).
De Taeye et al., Plasminogen activator inhibitor-1: a common denominator in obesity, diabetes and cardiovascular disease. Curr. Opin. Pharmacol. 5: 149-54 (2005).
Deng et al., Is plasminogen activator inhibitor-1 the molecular switch that governs urokinase receptor-mediated cell adhesion and release? J. Cell. Biol. 134: 1563-71 (1996).
Dichtl et al., In vivo stimulation by vascular plasminogen activator inhibitor-1 production by very low-density lipoprotein involves transcription factor binding to a VLDL-responsive element. *Thrombosis Haemastasis*, 84(4): 706-11 (2000).
Durand et al., Plasminogen activator inhibitor-I and tumour growth, invasion, and metastasis. Thromb. Haemost. 91: 438-49 (2004).
Ehrlich et al., Elucidation of structural requirements on plasminogen activator inhibitor 1 for binding to heparin. J. Biol. Chem. 267: 11606-11 (1992).
Eitzman et al., Bleomycin-induced pulmonary fibrosis in transgenic mice that either lack or overexpress the murine plasminogen activator inhibitor-1 gene. J. Clin. Invest. 97: 232-7 (1996).
Eitzman et al., Lack of plasminogen activator inhibitor-1 effect in a transgenic mouse model of metastatic melanoma. Blood. 87: 4718-22 (1996).
Elokdah et al., Tiplaxtinin, a novel, orally efficacious inhibitor of plasminogen activator inhibitor-1: design, synthesis, and preclinical characterization. J. Med. Chem. 47: 3491-4 (2004).
Erickson et al., Detection and partial characterization of an inhibitor of plasminogen activator in human platelets. J. Clin. Invest. 74: 1465-72 (1984).
European Patent Application No. 18837391, Extended European Search Report, dated Mar. 11, 2021.
Farkas et al., The recycling of apolipoprotein E in primary cultures of mouse hepatocytes. Evidence for a physiologic connection to high density lipoprotein metabolism. J. Biol. Chem. 278: 9412-7 (2003).
Fay et al., Brief report: complete deficiency of plasminogen-activator inhibitor type 1 due to a frame-shift mutation. N. Engl. J. Med. 327: 1729-33 (1992).
Fay et al., Platelets inhibit fibrinolysis in vitro by both plasminogen activator inhibitor-1-dependent and -independent mechanisms. Blood. 83: 351-6 (1994).
Gaitatzis et al., Novel insights into siderophore formation in myxobacteria. *ChemBioChem*, 6:365-74 (2005).
Giltay et al., Visceral fat accumulation is an important determinant of PAI-1 levels in young, nonobese men and women: modulation by cross-sex hormone administration. Arterioscler. Thromb. Vasc. Biol. 18: 1716-22 (1998).
Gorlatova et al., Mechanism of inactivation of plasminogen activator inhibitor-1 by a small molecule inhibitor. J. Biol. Chem. 282: 9288-96 (2007).
Gottschling-Zeller et al., Troglitazone reduces plasminogen activator inhibitor-1 expression and secretion in cultured human adipocytes. Diabetologia. 43: 377-83 (2000).
Hagglof et al., The reactive-center loop of active PAI-1 is folded close to the protein core and can be partially inserted. J. Mol. Biol. 335: 823-32 (2004).
Hamsten et al., Increased plasma levels of a rapid inhibitor of tissue plasminogen activator in young survivors of myocardial infarction. N. Engl. J. Med. 313: 1557-63 (1985).
Hasty et al., The recycling of apolipoprotein E in macrophages: influence of HDL and apolipoprotein A-I. Lipid Res. 46: 1433-9 (2005).
Heeren et al., Recycling of apoprotein E is associated with cholesterol efflux and high density lipoprotein internalization. J. Biol. Chem. 278: 14370-8 (2003).
Hekman et al., Bovine plasminogen activator inhibitor 1: specificity determinations and comparison of the active, latent, and guanidine-activated forms. Biochemistry. 27: 2911-8 (1988).
Hekman et al., Endothelial cells produce a latent inhibitor of plasminogen activators that can be activated by denaturants. J. Biol. Chem. 260: 11581-7 (1985).
Hennan et al., Evaluation of PAI-039 [{1-benzyl-5-[4-(trifluoromethoxy)phenyl]-1H-indol-3-yl} (oxo)acetic acid], a novel plasminogen activator inhibitor-1 inhibitor, in a canine model of coronary artery thrombosis. J. Pharmacol. Exp. Ther. 314: 710-6 (2005).
Herz et al., LDL receptor-related protein internalizes and degrades uPA-PAI-1 complexes and is essential for embryo implantation. Cell. 71: 411-21 (1992).
Horn et al., Plasminogen activator inhibitor 1 contains a cryptic high affinity receptor binding site that is exposed upon complex formation with tissue-type plasminogen activator. Thromb. Haemost. 80: 822-8 (1998).
Huber et al., Implications of the three-dimensional structure of alpha 1-antitrypsin for structure and function of serpins. Biochemistry. 28: 8951-66 (1989).

(56) References Cited

OTHER PUBLICATIONS

Huber et al., Plasminogen activator inhibitor type-1 (part one): basic mechanisms, regulation, and role for thromboembolic disease. J. Thromb. Thrombolysis. 11: 183-93 (2001).
Huntington et al., Structure of a serpin-protease complex shows inhibition by deformation. Nature. 407: 923-6 (2000).
Huntington et al., The serpins: nature's molecular mousetraps. Sci. Prog. 84: 125-36 (2001).
Hussain et al., The mammalian low-density lipoprotein receptor family. Annu. Rev. Nutr. 19: 141-72 (1999).
Hynes et al., Hydroxylamine derivatives as potential inhibitors of nucleic acid synthesis, J. Med. Chem., 16(5):576-8 (1973).
International Application No. PCT/US2018/043998, International Search Report and Written Opinion, mailed Oct. 10, 2018.
Jensen et al., Inhibition of plasminogen activator inhibitor-1 binding to endocytosis receptors of the low-density-lipoprotein receptor family by a peptide isolated from a phage display library. *Biochem. J.* 399(3): 387-96 (2006).
Jensen et al., The vitronectin binding area of plasminogen activator inhibitor-1, mapped by mutagenesis and protection against an inactivating organochemical ligand. FEBS Lett. 521: 91-4 (2002).
Kannel, Overview of hemostatic factors involved in atherosclerotic cardiovascular disease. Lipids. 40: 1215-20 (2005).
Kazi et al., Structure—activity relationships of synthetic analogs of (−)-epigallocatechin-3-gallate as proteasome inhibitors, Anticancer Research, 24:943-54 (2004).
Keijer et al., On the target specificity of plasminogen activator inhibitor 1: the role of heparin, vitronectin, and the reactive site. Blood. 78: 1254-61 (1991).
Kockx et al., Apolipoprotein A-I-stimulated apolipoprotein E secretion from human macrophages is independent of cholesterol efflux. J. Biol. Chem. 279: 25966-77 (2004).
Kohler et al., Plasminogen-activator inhibitor type 1 and coronary artery disease. N. Engl. J. Med. 342: 1792-1801 (2000).
Krieger et al., Scavenger receptor class B type I is a multiligand HDL receptor that influences diverse physiologic systems. J. Clin. Invest. 108: 793-7 (2001).
Krishnamurti et al., Plasminogen activator inhibitor: a regulator of ancrod-induced fibrin deposition in rabbits et al., Blood. 69: 798 (1987).
Lambers et al., Activation of human endothelial cell-type plasminogen activator inhibitor (PAI-1) by negatively charged phospholipids. J. Biol. Chem. 262: 17492-6 (1987).
Lawrence et al., Characterization of the binding of different conformational forms of plasminogen activator inhibitor-1 to vitronectin. Implications for the regulation of pericellular proteolysis. J. Biol. Chem. 272: 7676-80 (1997).
Lawrence et al., Engineering plasminogen activator inhibitor 1 mutants with increased functional stability. Biochemistry. 33: 3643-8 (1994).
Lawrence et al., Inactivation of plasminogen activator inhibitor by oxidants. Biochemistry. 25: 6351-5 (1986).
Lawrence et al., Localization of vitronectin binding domain in plasminogen activator inhibitor-1. J. Biol. Chem. 269: 15223-8 (1994).
Lawrence et al., Molecular Basis of Thrombosis and Hemostasis, Marcel Dekker Inc., New York, 517-43 (1995).
Lawrence et al., Partitioning of serpin-proteinase reactions between stable inhibition and substrate cleavage is regulated by the rate of serpin reactive center loop insertion into beta-sheet A. J. Biol. Chem. 275: 5839-44 (2000).
Lawrence et al., Purification of active human plasminogen activator inhibitor 1 from *Escherichia coli*. Comparison with natural and recombinant forms purified from eucaryotic cells. Eur. J. Biochem. 186: 523-33 (1989).
Lawrence et al., Serpin reactive center loop mobility is required for inhibitor function but not for enzyme recognition. J. Biol. Chem. 269: 27657-62 (1994).
Lawrence et al., Serpin-protease complexes are trapped as stable acyl-enzyme intermediates. J. Biol. Chem. 270: 25309-12 (1995).
Lawrence et al., Structure-function studies of the SERPIN plasminogen activator inhibitor type 1. Analysis of chimeric strained loop mutants. J. Biol. Chem. 265: 20293-301 (1990).
Le Lay et al., Regulation of ABCA1 expression and cholesterol efflux during adipose differentiation of 3T3-L1 cells. J. Lipid Res. 44: 1499-1507 (2003).
Levi, Inhibition of plasminogen activator inhibitor-1 activity results in promotion of endogenous thrombolysis and inhibition of thrombus extension in models of experimental thrombosis. Circulation. 85: 305-12 (1992).
Levin et al., Conversion of the active to latent plasminogen activator inhibitor from human endothelial cells. Blood. 70: 1090-8 (1987).
Liang et al., Plasminogen activator inhibitor-1 modulates adipocyte differentiation. Am. J. Physiol. Endocrinol. Metab. 290: E103-13 (2006).
Lijnen et al., On the role of plasminogen activator inhibitor-1 in adipose tissue development and insulin resistance in mice. J. Thromb. Haemost. 3: 1174-9 (2005).
Lindahl et al., Stability of plasminogen activator inhibitor 1 (PAI-1). Thromb. Haemost. 62: 748-51 (1989).
Liu et al., Highly purified scavenger receptor class B, type I reconstituted into phosphatidylcholine/cholesterol liposomes mediates high affinity high density lipoprotein binding and selective lipid uptake. J. Biol. Chem. 277: 34125-35 (2002).
Lopes et al., PAI-1 polymorphisms modulate phenotypes associated with the metabolic syndrome in obese and diabetic Caucasian population. *Diabetologia*. 46(9): 1284-90 (2003).
Loskutoff et al., Detection of an unusually stable fibrinolytic inhibitor produced by bovine endothelial cells. Proc. Natl. Acad. Sci. USA. 80: 2956-60 (1983).
Loskutoff et al., The adipocyte and hemostatic balance in obesity: studies of PAI-1. Arterioscler. Thromb. Vasc. Biol. 18: 1-6 (1998).
Lundgren et al., Elaboration of type-1 plasminogen activator inhibitor from adipocytes. A potential pathogenetic link between obesity and cardiovascular disease. Circulation. 93: 106-10 (1996).
Lupu et al., Localization and production of plasminogen activator inhibitor-1 in human healthy and atherosclerotic arteries. Arterioscler. Thromb. 13: 1090-1100 (1993).
Ma et al., Prevention of obesity and insulin resistance in mice lacking plasminogen activator inhibitor 1. Diabetes. 53: 336-46 (2004).
Mavri et al., Impact of adipose tissue on plasma plasminogen activator inhibitor-1 in dieting obese women. Arterioscler. Thromb. Vasc. Biol. 19: 1582-7 (1999).
Minor et al., Plasminogen activator inhibitor type 1 promotes the self-association of vitronectin into complexes exhibiting altered incorporation into the extracellular matrix. J. Biol. Chem. 277: 10337-45 (2002).
Morange et al., Glucocorticoids and insulin promote plasminogen activator inhibitor 1 production by human adipose tissue. Diabetes. 48: 890-5 (1999).
Mottonen et al., Structural basis of latency in plasminogen activator inhibitor-1. Nature. 355: 270-3 (1992).
Naski et al., Kinetics of inactivation of alpha-thrombin by plasminogen activator inhibitor-1. Comparison of the effects of native and urea-treated forms of vitronectin. J. Biol. Chem. 268: 12367-72 (1993).
Nilsson et al., VLDL activation of plasminogen activator inhibitor-1 (PAI-1) expression: Involvement of the VLDL receptor. *J. Lipid Res.* 40(5): 913-9 (1999).
Nordt, Differential regulation by troglitazone of plasminogen activator inhibitor type 1 in human hepatic and vascular cells. J. Clin. Endocrin. Metabol. 85: 1563-8 (2000).
Ny et al., Cloning and sequence of a cDNA coding for the human beta-migrating endothelial-cell-type plasminogen activator inhibitor. Proc. Natl. Acad. Sci. USA. 83: 6776-80 (1986).
Ohashi et al., Reverse cholesterol transport and cholesterol efflux in atherosclerosis. QJM. 98: 845-56 (2005).
Petyunin et al., Amides and hydrazides of oxalic acid. IV. Hydrazides of N-substituted oxamic acids, Zhurnal Obshchei Khimii, 34(1):28-32 (1964). CAPLUS Accession No. 1964:60623.

(56) References Cited

OTHER PUBLICATIONS

Podor et al., Incorporation of vitronectin into fibrin clots. Evidence for a binding interaction between vitronectin and gamma A/gamma' fibrinogen. J. Biol. Chem. 277: 7520-8 (2002).
Podor et al., New insights into the size and stoichiometry of the plasminogen activator inhibitor type-1.vitronectin complex. J. Biol. Chem. 275: 25402-10 (2000).
Podor et al., Type 1 plasminogen activator inhibitor binds to fibrin via vitronectin. J. Biol. Chem. 275: 19788-94 (2000).
Pubchem AKOS005831248—Compound Summary, pp. 1-3 (Jun. 18, 2007).
Pubmed Compound Summary for CID 62533622, 'Roxusqsrdixgtl-Uhfffaoysa-N', US National Library of Medicine, Oct. 22, 2012, pp. 1-10 (p3).
Reilly, Both circulating and clot-bound plasminogen activator inhibitor-1 inhibit endogenous fibrinolysis in the rat. Arterioscler. and Thromb.. 11: 1276 (1991).
Renckens et al., The role of plasminogen activator inhibitor type 1 in the inflammatory response to local tissue injury. J. Thromb. Haemost. 3: 1018-25 (2005).
Robbie et al., Inhibitors of fibrinolysis are elevated in atherosclerotic plaque. Arterioscler. Thromb. Vasc. Biol. 16: 539-45 (1996).
Rodenburg et al., Binding of urokinase-type plasminogen activator-plasminogen activator inhibitor-1 complex to the endocytosis receptors alpha2-macroglobulin receptor/low-density lipoprotein receptor-related protein and very-low-density lipoprotein receptor involved basic residues in the inhibitor. *Biochem. J.* 329(Part 1): 55-63 (1998).
Rohlmann et al., Inducible inactivation of hepatic LRP gene by cre-mediated recombination confirms role of LRP in clearance of chylomicron remnants. J. Clin. Invest. 101: 689-95 (1998).
Ross et al., Atherosclerosis—an inflammatory disease. N. Engl. J. Med. 340: 115-26 (1999).
Ruiz et al., The apoE isoform binding properties of the VLDL receptor reveal marked differences from LRP and the LDL receptor. J. Lipid Res. 46: 1721-31 (2005).
Sakamoto et al., TNF-alpha and insulin, alone and synergistically, induce plasminogen activator inhibitor-1 expression in adipocytes. Am. J. Physiol. 276: C1391-7 (1999).
Samad et al., Distribution and regulation of plasminogen activator inhibitor-1 in murine adipose tissue in vivo. Induction by tumor necrosis factor-alpha and lipopolysaccharide. J. Clin. Invest. 97: 37-46 (1996).
Samad et al., Tissue distribution and regulation of plasminogen activator inhibitor-1 in obese mice. Mol. Med. 2: 568-82 (1996).
Samad et al., Mol. Med. 2: 568-82 (1996).
Sawicki et al., A composite CMV-IE enhancer/beta-actin promoter is ubiquitously expressed in mouse cutaneous epithelium. Exp. Cell Res. 244: 367-9 (1998).
Schafer et al., Disruption of the plasminogen activator inhibitor 1 gene reduces the adiposity and improves the metabolic profile of genetically obese and diabetic ob/ob mice. FASEB J. 15: 1840-2 (2001).
Schneiderman et al., Increased type 1 plasminogen activator inhibitor gene expression in atherosclerotic human arteries. Proc. Natl. Acad. Sci. USA. 89: 6998-7002 (1992).
Seiffert et al., Constitutive and regulated expression of vitronectin. Histol. Histopathol. 12: 787-97 (1997).
Seiffert et al., The cell adhesion domain in plasma vitronectin is cryptic. J. Biol. Chem. 272: 13705-10 (1997).
Sharp et al., The active conformation of plasminogen activator inhibitor 1, a target for drugs to control fibrinolysis and cell adhesion. Structure. 7: 111-8 (1999).
Sherman et al., Saturation mutagenesis of the plasminogen activator inhibitor-1 reactive center. J. Biol. Chem. 267: 7588-95 (1992).
Shimomura et al., Enhanced expression of PAI-1 in visceral fat: possible contributor to vascular disease in obesity. Nat. Med. 2: 800-803 (1996).
Smith et al., Pivotal role of PAI-1 in a murine model of hepatic vein thrombosis. Blood. 107: 132-4 (2006).

Sprengers et al., Plasminogen activator inhibitors. Blood. 69: 381-7 (1987).
Stefansson et al., Inhibition of angiogenesis in vivo by plasminogen activator inhibitor-1. J. Biol. Chem. 276: 8135-41 (2001).
Stefansson et al., Mutants of plasminogen activator inhibitor-1 designed to inhibit neutrophil elastase and cathepsin G are more effective in vivo than their endogenous inhibitors. J. Biol. Chem. 279: 29981-7 (2004).
Stefansson et al., Old dogs and new tricks: proteases, inhibitors, and cell migration. Sci. STKE. 2003: pe24 (2003).
Stefansson et al., Plasminogen activator inhibitor-1 and vitronectin promote the cellular clearance of thrombin by low density lipoprotein receptor-related proteins 1 and 2. J. Biol. Chem. 271: 8215-20 (1996).
Stefansson et al., Plasminogen activator inhibitor-1 contains a cryptic high affinity binding site for the low density lipoprotein receptor-related protein. J. Biol. Chem. 273: 6358-66 (1998).
Stefansson et al., Plasminogen activator inhibitor-1 in tumor growth, angiogenesis and vascular remodeling. Curr. Pharm. Des. 9: 1545-64 (2003).
Stefansson et al., The serpin PAI-1 inhibits cell migration by blocking integrin alpha V beta 3 binding to vitronectin. Nature. 383: 441-3 (1996).
Stewart et al., Synthesis of 3-nitro-L-tyrosine peptides by means of active polyester intermediates derived from the nitrophenol side chain, Australian J. Chem. 3293:661-7 (1979).
STN Registry Database (accessed Aug. 8, 2016).
Strandberg et al., The oxidative inactivation of plasminogen activator inhibitor type 1 results from a conformational change in the molecule and does not require the involvement of the P1' methionine. J. Biol. Chem. 266: 13852-8 (1991).
Suganami et al., A paracrine loop between adipocytes and macrophages aggravates inflammatory changes: role of free fatty acids and tumor necrosis factor alpha. Arterioscler. Thromb. Vasc. Biol. 25: 2062-8 (2005).
Supplemental Partial European Search Report, European application No. 13850232, mailed Jul. 6, 2016.
Takahashi et al., Purification and ATPase activity of human ABCA1. J. Biol. Chem. 281: 10760-8 (2006).
Takahashi et al., The very low density lipoprotein (VLDL) receptor—a peripheral lipoprotein receptor for remnant lipoproteins into fatty acid active tissues. Mol. Cell. Biochem. 248: 121-7 (2003).
Tomasini et al., Vitronectin. Prog. Hemost. Thromb. 10: 269-305 (1991).
Vague et al., Correlation between blood fibrinolytic activity, plasminogen activator inhibitor level, plasma insulin level, and relative body weight in normal and obese subjects. Metabolism. 35: 250-3 (1986).
Van Eck et al., Role of the macrophage very-low-density lipoprotein receptor in atherosclerotic lesion development. Artherosclerosis. 183: 230-7 (2005).
Van Mourik et al., Purification of an inhibitor of plasminogen activator (antiactivator) synthesized by endothelial cells. J. Biol. Chem. 259: 14914-21 (1984).
Vassiliou et al., A novel efflux-recapture process underlies the mechanism of high-density lipoprotein cholesteryl ester-selective uptake mediated by the low-density lipoprotein receptor-related protein. Arterioscler. Thromb. Vasc. Biol. 24: 1669-75 (2004).
Vaughan et al., Studies of recombinant plasminogen activator inhibitor-1 in rabbits. Pharmacokinetics and evidence for reactivation of latent plasminogen activator inhibitor-1 in vivo. Circ. Res. 67: 1281-6 (1990).
Vaughan, PAI-1 and atherothrombosis. J. Thromb. Haemost. 3: 1879-83 (2005).
Vezina et al., Apolipoprotein distribution in human lipoproteins separated by polyacrylamide gradient gel electrophoresis. J. Lipid Res. 29: 573-85 (1988).
Webb et al., Plasminogen activator inhibitor 1 functions as a urokinase response modifier at the level of cell signaling and thereby promotes MCF-7 cell growth. J. Cell. Biol. 152: 741-52 (2001).

(56) References Cited

OTHER PUBLICATIONS

Weisberg et al., Pharmacological inhibition and genetic deficiency of plasminogen activator inhibitor-1 attenuates angiotensin II/salt-induced aortic remodeling. Arterioscler. Thromb. Vasc. Biol. 25: 365-71 (2005).
Weiss et al., Neutrophils degrade subendothelial matrices in the presence of alpha-1-proteinase inhibitor. Cooperative use of lysosomal proteinases and oxygen metabolites. J. Clin. Invest. 73: 1297-1303 (1984).
Wilczynska et al., The inhibition mechanism of serpins. Evidence that the mobile reactive center loop is cleaved in the native protease-inhibitor complex. J. Biol. Chem. 270: 29652-5 (1995).
Xu et al., Apolipoproteins of HDL can directly mediate binding to the scavenger receptor SR-BI, an HDL receptor that mediates selective lipid uptake. J. Lipid Res. 38: 1289-98 (1997).
Xu et al., Conservation of critical functional domains in murine plasminogen activator inhibitor-1. J. Biol. Chem. 279: 17914-20 (2004).
Yepes et al., Plasminogen Activator Inhibitor-1, Hemostasis and Thrombosis: Basic Principles and Clinical Practice, Lippincott Williams & Wilkins, 365-80 (2006).
Zannis et al., Role of apoA-I, ABCA1, Lcat, and SR-BI in the biogenesis of Hdl. J. Mol. Med. 84: 276-94 (2006).
Zhou et al., How vitronectin binds PAI-1 to modulate fibrinolysis and cell migration. Nat. Struct. Biol. 10: 541-4 (2003).

\* cited by examiner

PLASMINOGEN ACTIVATOR INHIBITOR-1 (PAI-1) INHIBITOR AND METHOD OF USE

STATEMENT OF GOVERNMENT SUPPORT

This invention was made with government support under HL089407 awarded by the National Institutes of Health. The government has certain rights in the invention.

FIELD

Provided herein are compounds and methods for modulating plasminogen activator inhibitor-1 (PAI-1) activity. More particularly, the disclosure is directed to inhibitors of PAI-1 and the uses of such inhibitors in regulating PAI-1 activity. Also provided are uses of these inhibitors for the treatment of many diseases or disorders associated with PAI-1 activity. Such diseases or disorders include, but are not limited to, dysregulation of lipid metabolism, obesity, diabetes, polycystic ovary syndrome, bone loss induced by estrogen deficiency, fibrosis and fibrotic disease, inflammation, cell migration and migration-driven proliferation of cells, angiogenesis, and thrombosis. Such inhibitors are also contemplated to be useful for modulation of endogenous fibrinolysis, and in conjunction with pharmacologic thrombolysis.

BACKGROUND

Plasminogen activator inhibitor-1 (PAI-1) is a 50 kDa single-chain glycoprotein that is the principal inhibitor of both urokinase type plasminogen activator (uPA) and tissue type PA (tPA). PAI-1 inhibits tPA and uPA with second-order rate constants $\sim 10^7 \text{ M}^{-1} \text{ s}^{-1}$, a value that is 10-1000 times faster than the rates of PA inhibition by other PAIs. Moreover, approximately 70% of the total tPA in carefully collected normal human plasma is detected in complex with PAI-1, suggesting that inhibition of tPA by PAI-1 is a normal, ongoing process. PAI-1 can also directly inhibit plasmin. Thus, PAI-1 is the chief regulator of plasmin generation in vivo, and as such it appears to play an important role in both fibrotic and thrombotic disease. PAI-1 has three potential N-linked glycosylation sites and contains between 15 and 20% carbohydrate.

PAI-1 belongs to the Serine Protease Inhibitor super family (SERPIN), which is a gene family that includes many of the protease inhibitors found in blood, as well as other proteins with unrelated or unknown functions. Serpins are consumed in the process of protease inactivation and thus act as "suicide inhibitors." The association between a serpin and its target protease occurs at an amino acid residue, referred to as the "bait" residue, located on a surface loop of the serpin called the reactive center loop (RCL). The "bait" residue is also called the P1 residue, and is thought to mimic the normal substrate of the enzyme. Upon association of the P1 residue with the S1 site of a target protease, cleavage of the RCL occurs. This is coupled to a large conformational change in the serpin which involves rapid insertion of the RCL into the major structural feature of a serpin, β-sheet A. This results in tight docking of the protease to the serpin surface and to distortion of the enzyme structure, including its active site. RCL insertion also produces a large increase in serpin structural stability making the complex rigid and thus trapping the protease in a covalent acyl-enzyme complex with the serpin.

Native PAI-1 exists in at least two distinct conformations, an active form that is produced by cells and secreted, and an inactive or latent form that accumulates in cell culture medium over time. In blood and tissues, most of the PAI-1 is in the active form; however, in platelets both active and latent forms of PAI-1 are found. In active PAI-1, the RCL is exposed on the surface of the molecule, but upon reaction with a protease, the cleaved RCL integrates into the center of β sheet A. In the latent form, the RCL is intact, but instead of being exposed, the entire amino terminal side of the RCL is inserted as the central strand into the β sheet A. This accounts for the increased stability of latent PAI-1 as well as its lack of inhibitory activity.

Active PAI-1 spontaneously converts to the latent form with a half-life of one to two hours at 37° C., and latent PAI-1 can be converted back into the active form by treatment with denaturants. Negatively charged phospholipids can also convert latent PAI-1 to the active form, suggesting that cell surfaces may modulate PAI-1 activity. The observation that latent PAI-1 infused into rabbits is apparently converted to the active form is consistent with this hypothesis. The spontaneous reversible interconversion between the active and latent structures is unique for PAI-1 and distinguishes it from other serpins; however, the biological significance of the latent conformation remains unknown.

Other non-inhibitory forms of PAI-1 have also been identified. The first form results from oxidation of one or more critical methionine residues within active PAI-1. This form differs from latent PAI-1 in that it can be partially reactivated by an enzyme that specifically reduces oxidized methionine residues. Oxidative inactivation of PAI-1 may be an additional mechanism for the regulation of PAI-1, and oxygen radicals produced locally by neutrophils or other cells may inactivate PAI-1 and thus facilitate the generation of plasmin at sites of infection or in areas of tissue remodeling. PAI-1 also exists in two different cleaved forms. As noted above, PAI-1 in complex with a protease is cleaved in its RCL. Uncomplexed PAI-1 can also be found with its RCL cleaved, which can arise from dissociation of PAI-1-PA complexes or from cleavage of the RCL by a non-target protease at a site other than the P1. None of these forms of PAI-1 are able to inhibit protease activity; however, they may interact with other ligands.

The interaction of PAI-1 with non-protease ligands plays an essential role in PAI-1 function. PAI-1 binds with high affinity to heparin, the cell adhesion protein vitronectin, and members the endocytic low-density lipoprotein receptor (LDL-R) family, such as the lipoprotein receptor-related protein (LRP), and the very low density lipoprotein receptor (VLDL-R). These non-protease interactions are important for both PAI-1 localization and function, and they are largely conformationally controlled through structural changes associated with RCL insertion. In blood, most of the active PAI-1 circulates in complex with the glycoprotein vitronectin. The PAI-1 binding site for vitronectin has been localized to a region on the edge of β-sheet A in the PAI-1 structure. The binding site for LDL-R family members is less well characterized, but has been identified, in a region of PAI-1 associated with alpha helix D that is adjacent to the vitronectin binding domain. The heparin binding domain on PAI-1 has also been mapped. This site also localizes to alpha helix D in a region homologous to the heparin binding domain of antithrombin III, and may overlap with the binding site for LDL-R family members.

Vitronectin circulates in plasma and is present in the extracellular matrix primarily at sites of injury or remodeling. PAI-1 and vitronectin appear to have a significant functional interdependence. Vitronectin stabilizes PAI-1 in its active conformation, thereby increasing its biological half-life.

Vitronectin also enhances PAI-1 inhibitory efficiency for thrombin approximately 300-fold. In turn, PAI-1 binding to vitronectin alters its conformation from the native plasma form, which does not support cell adhesion, to an "activated" form that is competent to bind integrins. However, integrin binding is blocked by the presence of PAI-1. As noted above, the association of PAI-1 with vitronectin is conformationally controlled and upon inhibition of a protease, the conformational change in PAI-1 associated with RCL insertion results in a loss of high affinity for vitronectin and a gain in affinity for LDL-R family members. This is due to RCL insertion in PAI-1, disrupting the vitronectin binding site, while simultaneously exposing a cryptic receptor binding site that is revealed only when PAI-1 is in a complex with a protease, which results in an approximately 100,000-fold shift in the relative affinity of PAI-1 from vitronectin to LDL-R family members and a subsequent shift in PAI-1 localization from vitronectin to the cellular receptor. Thus, PAI-1 association with vitronectin and LDL-R is conformationally controlled.

High PAI-1 levels are associated with various diseases and disorders. For example, high PAI-1 levels are associated with acute diseases, such as sepsis and myocardial infarction, and chronic disorders, such as cancer, atherosclerosis, and type 2 diabetes. In addition, high PAI-1 levels are associated with cardiovascular disease, wherein PAI-1 expression is significantly increased in severely atherosclerotic vessels, and PAI-1 protein levels rise consistently during disease progression from normal vessels to fatty streaks to atherosclerotic plaques. Increased PAI-1 levels are also linked to obesity, and insulin resistance.

In addition, elevated plasma levels of PAI-1 have been associated with thrombotic events, and antibody neutralization of PAI-1 activity resulted in promotion of endogenous thrombolysis and reperfusion. Elevated levels of PAI-1 have also been implicated in polycystic ovary syndrome and bone loss induced by estrogen deficiency.

PAI-1 is synthesized in both murine and human adipocytes. There is also a strong correlation between the amount of visceral fat and plasma levels of PAI-1 in humans and mice. This dramatic up-regulation of PAI-1 in obesity has led to the suggestion that adipose tissue itself may directly contribute to elevated systemic PAI-1, which in-turn increases the probability of vascular disease through increased thrombosis, and accelerated atherosclerosis. Notably, very recent data suggests that PAI-1 may also play a direct role in obesity.

In one study, genetically obese and diabetic ob/ob mice crossed into a PAI-1 deficient background had significantly reduced body weight and improved metabolic profiles compared to ob/ob mice with PAI-1. Likewise, nutritionally-induced obesity and insulin resistance were dramatically attenuated in mice genetically deficient in PAI-1 and in mice treated with an orally active PAI-1 inhibitor. The improved adiposity and insulin resistance in PAI-1-deficient mice may be related to the observation that PAI-1 deficient mice on a high fat diet had increased metabolic rates and total energy expenditure compared to wild-type mice, and peroxysome proliferator-activated receptor (PPARγ) and adiponectin were maintained. However, the precise mechanism involved was not shown and may be complex, since the over-expression of PAI-1 in mice also impaired adipose tissue formation. Taken together, these observations suggest that PAI-1 plays a previously unrecognized direct role in obesity and insulin resistance that involves interactions beyond its identified activities of modulating fibrinolysis and tissue remodeling.

Indeed, if PAI-1 positively regulates adipose tissue development, then the association of increased PAI-1 expression with developing obesity may constitute a positive feedback loop promoting adipose tissue expansion and dysregulation of normal cholesterol homeostasis. Thus, there exists a need in the art for a greater understanding of how PAI-1 is involved in metabolism, obesity and insulin resistance.

SUMMARY

Provided herein is a compound having a structure of

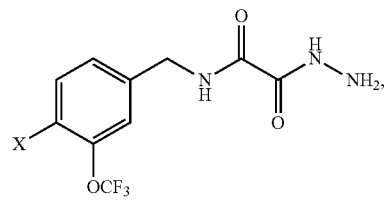

wherein X is Cl or F, or a pharmaceutically acceptable salt thereof. In some cases, the compound is

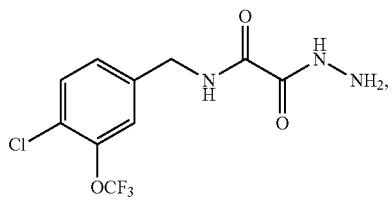 [SMILES: NNC(=O)C(=O)NCc1ccc(Cl)c(OC(F)(F)F)c1]

or a pharmaceutically acceptable salt thereof. In some cases, the compound is

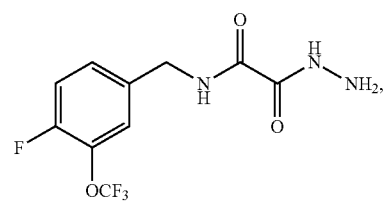 [SMILES: NNC(=O)C(=O)NCc1ccc(F)c(OC(F)(F)F)c1]

or a pharmaceutically acceptable salt thereof. Also provided is a PAI-1 inhibitor having a structure

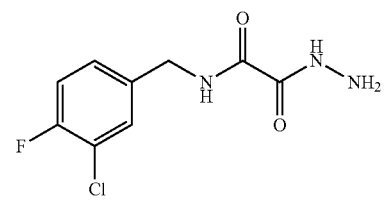 [SMILES: NNC(=O)C(=O)NCc1ccc(F)c(Cl)c1]

or a pharmaceutically acceptable salt thereof. Further provided is a PAI-1 inhibitor having a structure

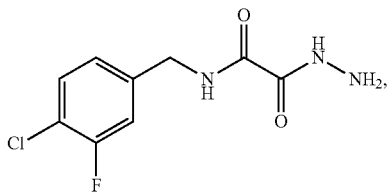 [SMILES: NNC(=O)C(=O)NCc1ccc(Cl)c(F)c1]

or a pharmaceutically acceptable salt thereof. In some cases, the compound is in the form of a pharmaceutically acceptable salt. Further provided are pharmaceutical compositions of one or more of the compounds or salts disclosed herein and a pharmaceutically acceptable excipient. In some cases, the composition comprises a compound having a structure of

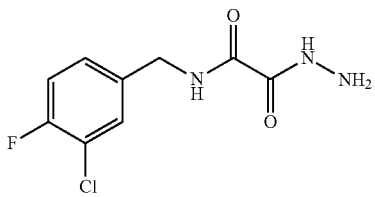 [SMILES: NNC(=O)C(=O)NCc1ccc(F)c(Cl)c1]

or pharmaceutically acceptable salt thereof. In some cases, the composition comprises a compound having a structure

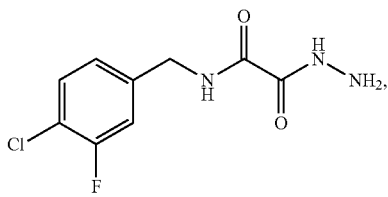 [SMILES: NNC(=O)C(=O)NCc1ccc(Cl)c(F)c1]

or a pharmaceutically acceptable salt thereof.

Further provided are methods of inhibiting PAI-1 by contacting PAI-1 with a compound as disclosed herein. Also provided are methods of treating a disorder associated with aberrant PAI-1 activity comprising administering to a subject in need thereof a compound as disclosed herein in an amount effective to treat the disorder. In some cases, the disorder is cancer, septicemia, obesity, insulin resistance, a disease or disorder associated with dysregulation of lipid metabolism, a disease or disorder associated with an elevated level of VLDL or LDL, high cholesterol, a proliferative disease or disorder, fibrosis and fibrotic disease, inflammatory bowel disease, coagulation homeostasis, cerebrovascular disease, microvascular disease, hypertension, dementia, atherosclerosis, osteoporosis, osteopenia, arthritis, asthma, heart failure, arrhythmia, angina, hormone insufficiency, Alzheimer's disease, hypertension, inflammation, sepsis, fibrinolytic disorder, stroke, dementia, coronary heart disease, myocardial infarction, stable and unstable angina, vascular disease, peripheral arterial disease, acute vascular syndrome, thrombosis, prothrombosis, deep vein thrombosis, pulmonary embolism, cerebrovascular disease, microvascular disease, hypertension, diabetes, hyperglycemia, hyperinsulinemia, malignant lesions, premalignant lesions, gastrointestinal malignancies, liposarcoma, epithelial tumor, and psoriasis, an extracellular matrix accumulation disorder, neoangiogenesis, myelofibrosis, fibrinolytic impairment, polycystic ovary syndrome, bone loss induced by estrogen deficiency, angiogenesis, neoangiogenesis, myelofibrosis, or fibrinolytic impairment. In various cases, the disease or disorder involving thrombosis or prothrombosis is formation of atherosclerotic plaques, venous thrombosis, arterial thrombosis, myocardial ischemia, atrial fibrillation, deep vein thrombosis, a coagulation syndrome, pulmonary thrombosis, cerebral thrombosis, a thromboembolic complication of surgery, and peripheral arterial occlusion. In some cases, the disorder is fibrosis, and more particularly, can be pulmonary fibrosis, renal fibrosis, cardiac fibrosis, hepatic fibrosis, or scleroderma. In some cases, the disorder is inflammatory bowel disease, and more particularly, can be Crohn's disease or ulcerative colitis. In some cases, the extracellular matrix accumulation disorder is renal fibrosis, chronic obstructive pulmonary disease, polycystic ovary syndrome, restenosis, renovascular disease, diabetic nephropathy, or organ transplant rejection.

Further provided are methods of modulating cholesterol, lipid clearance, and/or lipid uptake in a subject with an elevated level of PAI-1 comprising administering to the subject an effective amount of a compound disclosed herein in an amount effective to decrease the elevated level of PAI and modulate cholesterol, lipid clearance, and/or lipid uptake in the subject. In some cases, the compound increases circulating high density lipoprotein (HDL) and/or decreases circulating very low density lipoprotein (VLDL) in the subject. In various cases, the compound inhibits apolipoprotein E (ApoE) or apolipoprotein A (ApoA) binding to VLDL-R. In various cases, the compound decreases HDL or apolipoprotein E (ApoE) or apolipoprotein A (ApoA) binding to an ApoA receptor. In various cases, the compound decreases PAI-1 binding to apolipoprotein E (ApoE). In various cases, the compound decreases PAI-1 binding to apolipoprotein A (ApoA). In various cases, the compound decreases PAI-1 binding to VLDL. In various cases, the compound binds to PAI-1 in the presence of vitronectin. In various cases, the compound binds to PAI-1 in the presence of urokinase type plasminogen activator (uPA).

In any of the methods disclosed herein, the subject can be human.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

DETAILED DESCRIPTION

Figure 1:
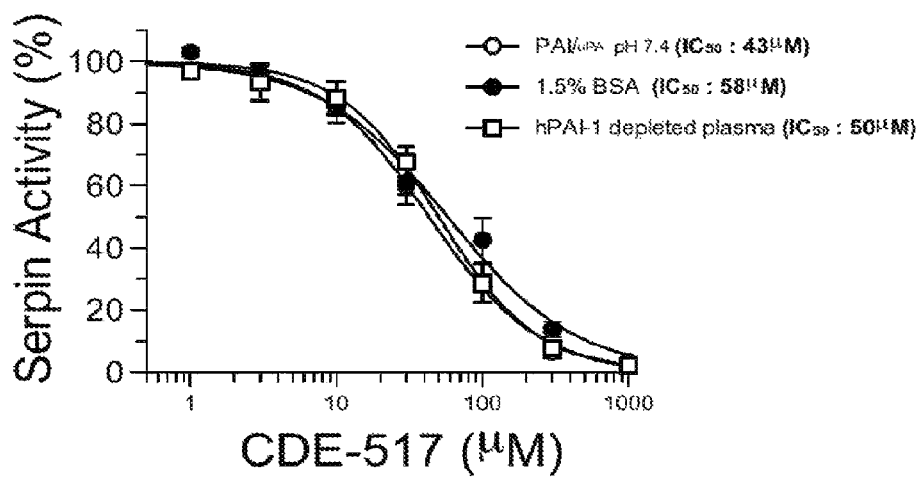
FIG. 1 shows the Serpin activity in the presence of various concentrations of CDE-517.

Provided herein is a PAI-1 inhibitor having a structure:

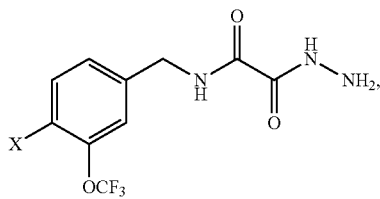

wherein X is Cl or F, or a pharmaceutically acceptable salt thereof. In some cases, the compound has a structure

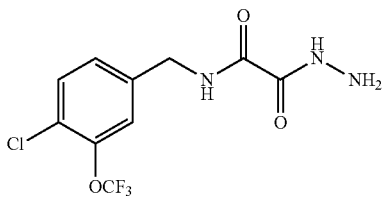 [SMILES: NNC(=O)C(=O)NCc1ccc(Cl)c(OC(F)(F)F)c1]

or a pharmaceutically acceptable salt thereof. In some cases, the compound has a structure

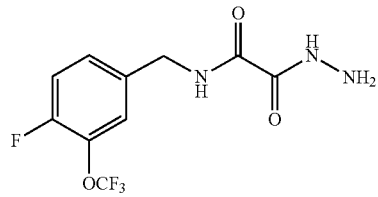 [SMILES: NNC(=O)C(=O)NCc1ccc(F)c(OC(F)(F)F)c1]

or a pharmaceutically acceptable salt thereof. Further provided is a PAI-1 inhibitor having a structure

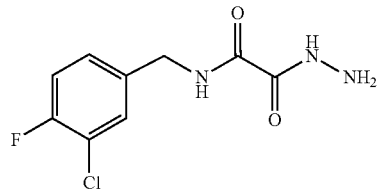 [SMILES: NNC(=O)C(=O)NCc1ccc(F)c(Cl)c1]

or a pharmaceutically acceptable salt thereof. Further provided is a PAI-1 inhibitor having a structure

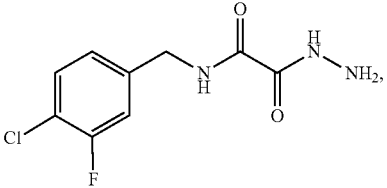 [SMILES: NNC(=O)C(=O)NCc1ccc(Cl)c(F)c1]

or a pharmaceutically acceptable salt thereof. Also provided are pharmaceutical compositions comprising one or more of these compounds or a salt thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al. describe pharmaceutically acceptable salts in detail in *J. Pharmaceutical Sciences,* 1977, 66, 1-19, which is incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, glutamate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts of compounds containing a carboxylic acid or other acidic functional group can be prepared by reacting with a suitable base. Such salts include, but are not limited to, alkali metal, alkaline earth metal, aluminum salts, ammonium, $N^+(C_{1-4}alkyl)_4$ salts, and salts of organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bis-dehydroabietylamine, glucamine, N-methylglucamine, collidine, quinine, quinoline, and basic amino acids such as lysine and arginine. This disclosure also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Methods of Using PAI-1 Inhibitors

As mentioned herein above, it is contemplated that methods disclosed herein include treating a disease or disorder associated with elevated levels of PAI-1 comprising administering a PAI-1 inhibitor. In one aspect, the subject is a mammal. In some cases, the mammalian subject is human.

In some embodiments, provided herein are PAI-1 inhibitor compounds and methods of using the compounds in the treatment of many diseases or disorders associated with PAI-1 activity. Such conditions, e.g., diseases or disorders, include, but are not limited to, dysregulation of lipid metabolism, obesity, diabetes, polycystic ovary syndrome, bone loss induced by estrogen deficiency, fibrosis and fibrotic disease, inflammation, cell migration and migration-driven proliferation of cells, and angiogenesis or thrombosis. In some aspects, such inhibitors are also contemplated to be useful for modulation of endogenous fibrinolysis, and in conjunction with pharmacologic thrombolysis. In various aspects, provided herein are PAI-1 inhibitor compounds and methods of using the compounds in the treatment of acute diseases associated with high PAI-1 levels, such as, but not limited to, sepsis, myocardial infarction, and thrombosis, compared to PAI-1 levels in normal subjects known not to suffer from sepsis, myocardial infarction, or thrombosis. In some aspects, the PAI-1 inhibitor compounds disclosed herein are used in methods for treating diseases and disorders associated with high PAI-1 levels, such as, but not limited to, cancer, atherosclerosis, insulin resistance, type 2 diabetes, and fibrotic diseases compared to PAI-1 levels in normal subjects known not to suffer from these diseases or disorders. In various aspects, provided herein are PAI-1 inhibitor compounds for regulating lipid metabolism, including increasing circulating HDL and/or decreasing circulating VLDL in a subject.

In various aspects, a PAI-1 inhibitor is useful in the treatment of any condition, including a disease or disorder, wherein the lowering of PAI-1 levels will provide benefits. The PAI-1 inhibitor is useful alone, or in combination with other compounds, which may act as to promote the reduction of PAI-1 levels.

The PAI-1 inhibitor can be formulated into an appropriate preparation and administered to one or more sites within the subject in a therapeutically effective amount. In some embodiments, the PAI-1 inhibitor-based therapy is effected via continuous or intermittent intravenous administration. In various aspects, the PAI-1 inhibitor-based therapy is effected via continuous or intermittent intramuscular or subcutaneous administration. In other aspects, the PAI inhibitor-based therapy is effected via oral or buccal administration. By "effective amount" what is meant is an amount of PAI-1 inhibitor compound that is sufficient to support an observable change in the level of one or more biological activities of PAI-1, plasminogen activator, HDL, LDL, or VLDL and/or an observable change in an indication for which the method of treatment is intended. The change may be reduced level of PAI-1 activity. In some aspects, the change is an increase in plasminogen activator, and/or HDL and/or a reduction in LDL and VLDL.

In various aspects, administration of the compositions is systemic or local, and in still other aspects comprises a single site injection of a therapeutically-effective amount of the PAI-1 inhibitor composition. Any route known to those of skill in the art for the administration of a therapeutic composition disclosed herein is contemplated including, for example, intravenous, intramuscular, subcutaneous, oral, or a catheter for long-term administration.

In some cases, it is contemplated that the therapeutic composition is delivered to the patient at multiple sites. The multiple administrations are rendered simultaneously or are administered over a period of several hours. It is likewise contemplated that the therapeutic composition is taken on a regular basis via oral administration. In certain cases, it is beneficial to provide a continuous flow of the therapeutic composition. Additional therapy is administered on a period basis, for example, daily, weekly, or monthly.

In addition to therapies based solely on the delivery of the PAI-1 inhibitor composition, combination therapy is specifically contemplated. It is contemplated that the PAI-1 inhibitor composition therapy is used similarly in conjunction with other agents commonly used for the treatment of elevated levels of PAI-1, LDL and VLDL.

To achieve the appropriate therapeutic outcome, using the methods and compositions disclosed herein, it is further contemplated that a composition comprising a PAI-1 inhibitor and at least one other therapeutic agent (second therapeutic agent) is administered to a subject in need thereof. Such therapeutic agents include drugs used to manage cardiovascular disease including, but not limited to, cholesterol lowering drugs, such as statins, anti-inflammatories, and ACE inhibitors. Such drugs also include drugs targeting neurological disorders including, but not limited to drugs for targeting stroke, seizures, and Alzheimer's Disease. In another aspect, the additional agents include, but are not limited to, drugs targeting diabetes. These are all disorders associated with elevated levels of PAI-1 and, therefore, it is contemplated that combination therapy may be used with PAI-1 inhibitors and other known therapies.

The combination therapy compositions are provided in a combined amount effective to produce the desired therapeutic outcome in the treatment of increased levels of PAI-1, VLDL, or LDL and/or make a detectable change in an indication as described herein. This process involves administering the PAI-1 inhibitor and the second agent(s) or factor(s) at the same time. Methods thus include administering a single composition or pharmacological formulation that includes both agents, or administering two distinct compositions or formulations, at the same time, wherein one composition includes the PAI-1 inhibitor therapeutic composition and the other includes the second therapeutic agent.

Alternatively, the PAI-1 inhibitor treatment precedes or follows the second therapeutic agent treatment by intervals ranging from minutes to weeks. In embodiments where the second therapeutic agent and the PAI-1 inhibitor are administered separately, one generally ensures that a significant period of time did not expire between the times of each delivery, such that the second therapeutic agent and the PAI-1 inhibitor are able to exert an advantageously combined effect. In such instances, it is contemplated that one administers both modalities within about 12-24 hours of each other, or alternately, within about 6-12 hours of each other, or alternately, with a delay time of only about 12 hours. In some situations, it is desirable to extend the time period for treatment significantly, however, where several days (2, 3, 4, 5, 6 or 7) to several weeks (1, 2, 3, 4, 5, 6, 7 or 8) lapse between the respective administrations.

Systemic delivery of PAI-1 inhibitors to patients is a very efficient method for delivering a therapeutically effective amount of the compound to counteract the immediate clinical manifestations of a disease or disorder. Alternatively, local delivery of the PAI-1 inhibitor and/or the second therapeutic agent is appropriate in certain circumstances. In a certain embodiment, it is contemplated that the PAI-1 inhibitor is delivered to a patient for an extended period of time. It is further contemplated that the PAI-1 inhibitor is taken throughout a patient's lifetime to lower PAI-1, VLDL and/or LDL levels.

Pharmaceutical Compositions

As mentioned herein above, provided herein are methods using pharmaceutical compositions comprising effective amounts of PAI-1 inhibitor together with pharmaceutically acceptable excipient, such as diluents, preservatives, solubilizers, emulsifiers, adjuvants and/or carriers useful in PAI-1 inhibitor therapy. Such compositions include diluents of various buffer content (e.g., Tris-HCl, acetate, phosphate), pH and ionic strength; additives such as detergents and solubilizing agents (e.g., Tween 80, Polysorbate 80), antioxidants (e.g., ascorbic acid, sodium metabisulfite), preservatives (e.g., thimersol, benzyl alcohol), and bulking substances (e.g., lactose, mannitol); incorporation of the material into particulate preparations of polymeric compounds, such as polylactic acid, polyglycolic acid, etc., or in association with liposomes or micelles. Such compositions will influence the physical state, stability, rate of in vivo release, and rate of in vivo clearance of the PAI-1 inhibitor. See, e.g., Remington's Pharmaceutical Sciences, 18th Ed. (1990) Mack Publishing Co., Easton, PA, pages 1435-1712, which are herein incorporated by reference.

Sterile liquid compositions include solutions, suspensions, emulsions, syrups and elixirs. The compounds disclosed herein may be dissolved or suspended in the pharmaceutically acceptable carrier, such as sterile water, sterile organic solvent or a mixture of both. In one aspect, the liquid carrier is one suitable for parental injection. Where the compounds are sufficiently soluble they can be dissolved directly in normal saline with or without the use of suitable organic solvents, such as propylene glycol or polyethylene glycol. If desired, dispersions of the finely divided compounds can be made-up in aqueous starch or sodium carboxymethyl cellulose solution, or in a suitable oil, such as *arachis* oil. Liquid pharmaceutical compositions, which are sterile solutions or suspensions, can be utilized by intramuscular, intraperitoneal or subcutaneous injection. In many instances a liquid composition form may be used instead of the preferred solid oral method of administration.

It is preferred to prepare unit dosage forms of the compounds for standard administration regimens. In this way, the composition can be subdivided readily into smaller doses at the physician's direction. For example, unit dosages may be made up in packeted powders, vials or ampoules and, in one aspect, in capsule or tablet form. The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analysis and the patient's recovery rate.

The precise dosage to be employed depends upon several factors including the host, whether in veterinary medicine or human medicine, the nature and severity of the condition, e.g., disease or disorder, being treated, the mode of administration and the particular active substance employed. The compounds may be administered by any conventional route, in particular enterally, and, in one aspect, orally in the form of tablets or capsules. Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure, stroke, peripheral arterial occlusion, and related disease states). These measures will slow the rate of progress of the disease state and assist the body in reversing the process direction in a natural manner.

PAI-1 inhibitors or derivatives thereof may be formulated for injection, or oral, nasal, pulmonary, topical, or other types of administration as one skilled in the art will recognize. The formulation may be liquid or may be solid, such as lyophilized, for reconstitution.

PAI-1 inhibitor or derivatives thereof are useful in the treatment of any of the acute or chronic diseases or disorders associated with increased levels of PAI-1, LDL, or VLDL. Conditions (e.g., diseases or disorders) alleviated or modulated by the administration of PAI-1 inhibitor, in some aspects, are those characterized by increased levels of VLDL and LDL. Such conditions may be induced as a course of therapy for other purposes, such as chemotherapy or radiation therapy. It is contemplated that such conditions may result from genetic inheritance or be the side effect of another condition or medication.

The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well-known in the art. Except insofar as any conventional media or agent is incompatible with the vectors or cells, its use in therapeutic compositions is contemplated. Supplementary active ingredients also can be incorporated into the compositions.

The active compositions used in the methods disclosed herein include classic pharmaceutical preparations. Administration of these compositions will be via any common route so long as the target tissue is available via that route. The pharmaceutical compositions may be introduced into the subject by any conventional method, e.g., by intravenous, intradermal, intramusclar, intramammary, intraperitoneal, intrathecal, retrobulbar, intrapulmonary (e.g., term release); by oral, sublingual, nasal, anal, vaginal, or transdermal delivery, or by surgical implantation at a particular site. The treatment may consist of a single dose or a plurality of doses over a period of time.

The active compounds may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents (for example, sugars or sodium chloride). Prolonged absorption of the injectable compositions can be brought about by the use in the compositions of agents delaying absorption (for example, aluminum monostearate and gelatin).

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum-drying and freeze-drying techniques that yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well-known in the art. Except insofar as any conventional media or agent is incompatible with the active ingredient, its use in the therapeutic compositions is contemplated. Supplementary active ingredients also can be incorporated into the compositions.

For oral administration of the compositions, a PAI-1 inhibitor may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions used in the methods may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

The compositions used in the methods may be formulated in micelles or liposomes. Such formulations include sterically stabilized micelles or liposomes and sterically stabilized mixed micelles or liposomes. Such formulations can facilitate intracellular delivery, since lipid bilayers of liposomes and micelles are known to fuse with the plasma membrane of cells and deliver entrapped contents into the intracellular compartment.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

Generally, an effective amount of a PAI-1 inhibitor, or derivatives thereof, will be determined by the age, weight, and condition or severity of disease or disorder of the recipient. See, Remington's Pharmaceutical Sciences, supra, pages 697-773, herein incorporated by reference. Typically, a dosage of between about 0.001 µg/kg body weight/day to about 1000 µg/kg body weight/day, may be used, but more or less, as a skilled practitioner will recognize, may be used. Dosing may be one or more times daily, or less frequently, and may be in conjunction with other compositions as described herein. It should be noted that the disclosure is not limited to the dosages recited herein.

By initiating the treatment regimen with a minimal daily dose of about one gram, the blood levels of PAI-1 and the patient's symptomatic relief analysis may be used to determine whether a larger dose is indicated. One skilled in the art will appreciate that the appropriate dosage levels for treatment will thus vary depending, in part, upon the molecule delivered, the indication for which the PAI-1 inhibitor compound is being used, the route of administration, and the size (body weight, body surface or organ size) and condition (the age and general health) of the patient. Accordingly, the clinician may titer the dosage and may modify the route of administration to obtain the optimal therapeutic effect. A typical dosage may range from about 0.1 µg/kg to up to about 100 mg/kg or more, depending on the factors mentioned above. In other embodiments, the dosage may range from 0.1 µg/kg up to about 100 mg/kg; or 1 µg/kg up to about 100 mg/kg; or 5 µg/kg up to about 100 mg/kg.

"Unit dose" is defined as a discrete amount of a therapeutic composition dispersed in a suitable carrier. Parenteral administration may be carried out with an initial bolus followed by continuous infusion to maintain therapeutic circulating levels of drug product. Those of ordinary skill in the art will readily optimize effective dosages and administration regimens as determined by good medical practice and the clinical condition of the individual patient.

The frequency of dosing will depend on the pharmacokinetic parameters of the agents and the routes of administration. The optimal pharmaceutical formulation will be determined by one of skill in the art depending on the route of administration and the desired dosage. See, for example, Remington's Pharmaceutical Sciences, supra, pages 1435-1712, incorporated herein by reference. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein, as well as the pharmacokinetic data observed in animals or human clinical trials.

Appropriate dosages may be ascertained through the use of established assays for determining level of myocardial infarct in conjunction with relevant dose-response data. The final dosage regimen will be determined by the attending physician, considering factors that modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment.

It will be appreciated that the pharmaceutical compositions and treatment methods disclosed herein are useful in fields of human medicine and veterinary medicine. Thus the subject to be treated is in one aspect a mammal. In another aspect, the mammal is a human.

In addition, further contemplated is a kit containing components comprising a composition comprising a PAI-1 inhibitor; and optionally, at least one additional factor useful in the treatment of the acute and chronic diseases and disorders discussed herein.

Uses of Compounds in the Treatment of Diseases or Disorders

Provided herein is the use of compounds as disclosed for the production of a medicament for the treatment or prevention of any disease or disorder discussed herein.

The compounds are inhibitors of the serine protease inhibitor PAI-1, and are therefore useful in the treatment or prophylaxis of those processes which involve the production and/or action of PAI-1. Thus, the compounds, in various aspects, are useful in preventing or reducing thrombosis, promoting thrombolysis, reducing fibrosis regulating lipid metabolism as described herein. In some aspects, the compounds are useful in treating high cholesterol and diseases or disorders associated with elevated levels of PAI-1. In various aspects, the compounds are useful in treating elevated levels of VLDL or LDL. In some aspects, the compounds are useful in elevating HDL.

In some aspects, provided are the uses of these inhibitors for the treatment of a disease or disorder associated with PAI-1 activity. Such diseases or disorders include, but are not limited to, inflammation, cell migration and migration-driven proliferation of cells, and angiogenesis or thrombosis. Such inhibitors are also contemplated to be useful for modulation of endogenous fibrinolysis, and in conjunction with pharmacologic thrombolysis.

The compounds are useful in the treatment or prevention of insulin resistance, obesity, non-insulin dependent diabetes mellitus, cardiovascular disease, thrombotic events associated with coronary artery and cerebrovascular disease. The compounds are also useful for inhibiting the disease process involving the thrombotic and prothrombotic states which include, but are not limited to, formation of atherosclerotic plaques, venous and arterial thrombosis, myocardial ischemia, atrial fibrillation, deep vein thrombosis, coagulation syndromes, pulmonary thrombosis, cerebral thrombosis, thromboembolic complications of surgery (such as joint replacement), and peripheral arterial occlusion. These compounds are also useful in treating stroke associated with or resulting from atrial fibrillation.

The compounds are also used in the treatment or prophylaxis of high cholesterol and diseases or disorders associated with such a condition.

The compounds may also be used in the treatment of diseases or disorders associated with extracellular matrix accumulation, including, but not limited to, renal fibrosis, chronic obstructive pulmonary disease, polycystic ovary syndrome, restenosis, renovascular disease and organ transplant rejection.

The compounds may also be used in the treatment of fibrosis, including, but not limited to, pulmonary fibrosis, renal fibrosis, cardiac fibrosis, hepatic fibrosis, and scleroderma.

The compounds may also be used in the treatment of inflammatory bowel disease, including, but not limited to, Crohn's disease and ulcerative colitis.

The compounds may also be used in the treatment of malignancies, and diseases or disorders associated with neoangiogenesis (such as diabetic retinopathy).

The compounds may also be used in conjunction with and following processes or procedures involving maintaining blood vessel patency, including vascular surgery, vascular graft and stent patency, organ, tissue and cell implantation and transplantation.

The compounds may also be used in the treatment of Alzheimer's disease. This method may also be characterized as the inhibition of plasminogen activator by PAI-1 in a mammal, particularly a human, experiencing or subject to Alzheimer's disease. This method may also be characterized as a method of increasing or normalizing levels of plasmin concentration in a mammal, particularly those experiencing or subject to Alzheimer's disease.

The compounds may be used for the treatment of myelofibrosis with myeloid metaplasia by regulating stromal cell hyperplasia and increases in extracellular matrix proteins.

The compounds may also be used in conjunction with protease inhibitor-containing highly active antiretroviral therapy (HAART) for the treatment of diseases or disorders which originate from fibrinolytic impairment and hypercoagulability of HIV-1 infected patients receiving such therapy.

The compounds may be used for the treatment of diabetic nephropathy and renal dialysis associated with nephropathy.

The compounds may be used to treat cancer, septicemia, proliferative diseases, such as psoriasis, improving coagulation homeostasis, cerebrovascular diseases, microvascular disease, hypertension, dementia, atherosclerosis, osteoporosis, arthritis, asthma, heart failure, arrhythmia, angina, and as a hormone replacement agent, treating, preventing or reversing progression of atherosclerosis, Alzheimer's disease, osteoporosis, osteopenia; reducing inflammatory markers, fibrinolytic disorder, reducing C-reactive protein, or preventing or treating low grade vascular inflammation, stroke, dementia, coronary heart disease, primary and secondary prevention of myocardial infarction, stable and unstable angina, primary prevention of coronary events, secondary prevention of cardiovascular events, peripheral vascular disease, peripheral arterial disease, acute vascular syndromes, deep vein thrombosis, pulmonary embolism, reducing the risk of undergoing a myocardial revascularization procedure, microvascular diseases such as nephropathy, neuropathy, retinopathy and nephrotic syndrome, hypertension, Type 1 and 2 diabetes and related diseases, obesity, insulin resistance, hyperglycemia, hyperinsulinemia, malignant lesions, premalignant lesions, gastrointestinal malignancies, liposarcomas and epithelial tumors, proliferative diseases such as psoriasis, improving coagulation homeostasis, and/or improving endothelial function, and all forms of cerebrovascular diseases.

The compounds disclosed herein can be used for the topical applications in wound healing for prevention of scarring.

The compounds disclosed herein can be used in the treatment of inflammatory diseases, septic shock and the vascular damage associated with infections and for the treatment of blood and blood products used in dialysis, blood storage in the fluid phase, especially ex vivo platelet aggregation. The compounds may also be used in combination with prothrombolytic, fibrinolytic and anticoagulant agents. The present compounds may also be added to human plasma during the analysis of blood chemistry in hospital settings to determine the fibrinolytic capacity thereof.

Further provided herein are methods for treating, preventing, ameliorating or inhibiting each of the maladies mentioned herein in a mammal, in one aspect, in a human, the method(s) each comprising administering to a mammal in need of such treatment, prevention, amelioration or inhibition a pharmaceutically or therapeutically effective amount of a compound disclosed herein, or a pharmaceutically acceptable salt thereof.

The compounds disclosed herein can also be used to treat cancer including, but not limited to, breast and ovarian cancer, and as imaging agents for the identification of metastatic cancers.

It will be understood that a pharmaceutically or therapeutically effective amount of a compound herein refers to an amount of the compound in question which will sufficiently inhibit the serine protease inhibitor PAI-1 in the mammal in need thereof to a sufficient extent to provide a desirable improvement in the condition in question or provide sufficient inhibition of the serine protease inhibitor PAI-1 to prevent, inhibit or limit the onset of the physiological basis for the malady or condition in question.

EXAMPLES

Synthesis of Compound CDE 517:

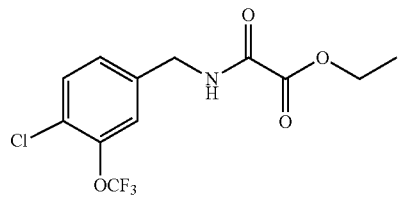 [SMILES: CCOC(=O)C(=O)NCc1ccc(Cl)c(OC(F)(F)F)c1]

Ethyl 2-((4-chloro-3-(trifluoromethoxy)benzyl)amino)-2-oxoacetate: A stirring solution of 4-chloro-3-(trifluoromethoxy)benzylamine (771.9 mg, 3.42 mmol) and pyridine (830 μL, 10.26 mmol) in dichloromethane (10 mL) was cooled in an ice bath. Ethyl oxalyl chloride (385 μL, 3.42 mmol) was added dropwise and the mixture was stirred for 24 hours at room temperature. The reaction mixture was diluted with ethyl acetate and washed with 0.2N HCl (2×), saturated aqueous $NaHCO_3$ (2×), and brine (1×). The organic layer was dried over magnesium sulfate, filtered, and concentrated in vacuo to afford 1.0726 g (96% yield) of product as a clear oil. $^1$H-NMR (DMSO-$d_6$, 400 MHz) δ 9.5 (t, J=6 Hz, 1H), 7.62 (d, J=8.2 Hz, 1H), 7.44 (bs, 1H), 7.3 (dd, J=8.7, 1.8 Hz, 1H), 4.33 (d, J=6.4 Hz, 2H), 4.21 (q, J=6.9 Hz, 2H), 1.23 (t, J=6.9 Hz, 3H).

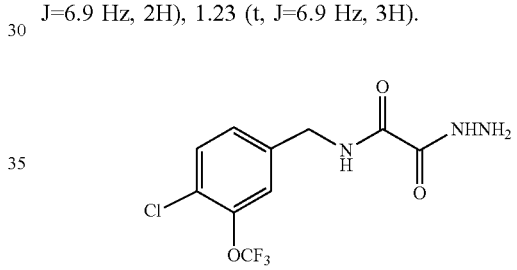

N-(4-chloro-3-(trifluoromethoxy)benzyl)-2-hydrazinyl-2-oxoacetamide (CDE-517): To a solution of ethyl 2-((4-chloro-3-(trifluoromethoxy)benzyl)amino)-2-oxoacetate (1.0726 g, 3.29 mmol) in absolute ethanol (30 mL) was added 50% hydrazine hydrate (425 μL, 6.59 mmol) dropwise and stirred for 2 hours. The solid was filtered, dried in vacuo, and then triturated with boiling deionized water to afford 0.7191 g (70.2% yield) of product as a white solid. $^1$H-NMR (DMSO-d6, 400 MHz) δ 10.1 (bs, 1H), 9.37 (t, J=6.4 Hz, 1H), 7.61 (d, J=8.2 Hz, 1H), 7.42 (bs, 1H), 7.28 (dd, J=8.3, 1.8 Hz, 1H), 4.5 (d, J=3.6 Hz, 2H), 4.31 (d, J=6.4 Hz, 2H); $^{13}$C-NMR (DMSO-d6, 100 MHz) δ 160.6, 158.3, 144.3, 141.1, 131.4, 128.5, 124.8, 122.4, 120.6 (q, J=256.5 Hz), 41.8.

Synthesis of Compound CDE-415:

N-(3-chloro-4-fluorobenzyl)-2-hydrazinyl-2-oxoacetamide (CDE-415): To a solution of 3-chloro-4-fluorobenzylamine (230 μL, 1.83 mmol) and pyridine (296 μL, 3.66 mmol) in dichloromethane (5 ml), ethyl 2-chloro-2-oxoacetate (215 □L, 1.92 mmol) was added dropwise over an ice bath. The solution was removed from the ice bath after 5 minutes and left to warm to room temperature. The reaction mixture was diluted with ethyl acetate, washed with 0.2 N HCl (2×) and saturated $NaHCO_3$ (1×), dried with $MgSO_4$, filtered and concentrated in vacuo to give 0.336 g of ethyl 2-(3-chloro-4-fluorobenzylamino)-2-oxoacetate as a white solid (71% yield). $^1$H NMR (CDCl$_3$, 400 MHz) δ 7.42 (s, 1H), 7.34 (dd, J=2.3, 6.9 Hz, 1H), 7.17 (M, 1H), 7.10 (t, J=8.7 Hz, 1H), 4.46 (d, J=6.0 Hz, 2H), 4.35 (q, J=7.3 Hz, 2H), 1.39 (t, J=6.9 Hz, 3H). To a solution of ethyl 2-(3-chloro-4-fluorobenzylamino)-2-oxoacetate (211.9 mg, 0.816 mmol) in ethanol (6 ml), 50% hydrazine hydrate (102 µL) was added dropwise. The reaction was stirred overnight at room temperature. The product was filtered from the mixture and dried in vacuo, providing 0.188 g of N-(3-chloro-4-fluorobenzyl)-2-hydrazinyl-2-oxoacetamide as a white solid (94% yield). $^1$H NMR (DMSO-$d_6$, 400 MHz) δ 10.01 (s, 1H), 9.28 (t, J=6.4 Hz, 1H), 7.42 (dd, J=1.8, 5.5 Hz, 1H), 7.32 (t, J=8.7 Hz, 1H), 7.23 (m, 1H), 4.48 (s, 2H), 4.25 (d, J=6.4 Hz, 2H); $^{13}$C NMR (DMSO-$d_6$, 100 MHz) δ 160.48, 158.43, 156.75 (d, J=244 Hz), 137.32, 129.97, 128.63, 119.62 (J=18 Hz), 117.25 (J=20 Hz), 41.66.

Synthesis of Compound CDE-412:

N-(4-chloro-3-fluorobenzyl)-2-hydrazinyl-2-oxoacetamide (CDE-412): To a solution of 4-chloro-3-fluorobenzylamine (225 µL, 1.83 mmol) and pyridine (296 µL, 3.66 mmol) in dichloromethane (5 ml), ethyl 2-chloro-2-oxoacetate (215 □L, 1.92 mmol) was added dropwise over an ice bath. The solution was removed from the ice bath after 10 minutes and left to warm to room temperature. The reaction mixture was diluted with ethyl acetate, washed with 0.2 N HCl (2×) and saturated NaHCO$_3$ (1×), dried with MgSO$_4$, filtered and concentrated in vacuo to give 0.3878 g (82% yield) of ethyl 2-(4-chloro-3-fluorobenzylamino)-2-oxoacetate as a white solid. $^1$H NMR (CDCl$_3$, 400 MHz) δ 7.45 (s, 1H), 7.36 (t, J=7.96 Hz, 1H), 7.09 (d, J=9.6 Hz, 1H), 7.02 (d, J=8.3 Hz, 1H), 4.48 (d, J=6.4 Hz, 2H), 4.35 (q, J=6.9 Hz, 2H), 1.38 (t, J=6.9 Hz, 3H). To a solution of ethyl 2-(4-chloro-3-fluorobenzylamino)-2-oxoacetate (119.7 mg, 0.461 mmol) in ethanol (6 ml), 50% hydrazine hydrate (57 µL) was added dropwise. The reaction was stirred overnight at room temperature. The product was filtered from the mixture and dried in vacuo, providing 59.0 mg of N-(4-chloro-3-fluorobenzyl)-2-hydrazinyl-2-oxoacetamide as a white solid (52% yield). $^1$H NMR (DMSO-$d_6$, 400 MHz) δ 10.02 (s, 1H), 9.30 (t, J=6.4 Hz, 1H), 7.49 (t, J=8.24 Hz, 1H), 7.24 (dd, J=1.8, 10.5 Hz, 1H), 7.08 (dd, J=1.36, 8.24 Hz, 1H), 4.51 (s, 2H), 4.27 (d, J=6.4 Hz, 2H); $^{13}$C NMR (DMSO-$d_6$, 100 MHz) δ 160.54, 158.74, 158.40, 156.29, 141.29, 141.23, 130.99, 125.08, 125.05, 118.36, 118.19, 116.31, 116.10, 41.86.

Fluorometric IC50 plate assay for PAI-1 inhibitors: For assaying PAI-1 inhibitor activity in plasma, recombinant active human PAI-1 (Molecular Innovations) was added to PAI-1 depleted human plasma (Molecular Innovations) containing 10 µg/mL aprotinin (Roche) to a concentration 20 nM. Then 10 µL of this human plasma (with or without PAI-1) was added to wells containing 80 µL of buffer with increasing concentrations of the PAI-1 inhibitor (Buffer: 40 mM HEPES, 100 mM NaCl, 0.005% Tween-20, pH 7.4, and 10% DMSO) and incubated for 15 min at 23° C. Next, 10 µL of 25 nM UPA (rheotromb) (final 2.5 nM) was added to each reaction well and incubated for an additional 30 min at 24° C., the final PAI-1 concentration was 2 nM and the final uPA concentration was 2.5 nM. Following this incubation 100 µL of buffer containing 100 mM of the uPA fluorgenic substrate Z-Gly-Gly-Arg-AMC (Calbiochem) is added for a final concentration of 50 µM, and the residual uPA activity in each reaction mixture was determined from the rate of AMC release by uPA measured with an excitation wavelength of 370 nm and an emission wavelength of 440 nm for 10 minutes at 23° C. Data are expressed as the residual PAI-1 activity as a percent of the control PAI-1 activity.

For assays in buffer or buffer containing 1.5% bovine serum albumin (BSA) the assay was as above except that no plasma or aprotinin was added and activity was determined in either 100 mM NaCl, 40 mM HEPES, 0.005% Tween-20, 10% DMSO, pH 7.4, or in the same buffer containing 1.5% BSA. Results are shown in the figures. FIG. 1 is for a compound of structure

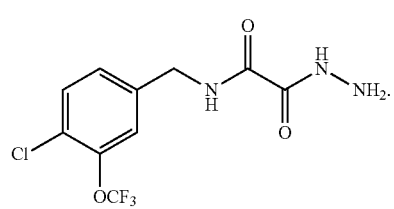

(CDE-517)

Figure 2:
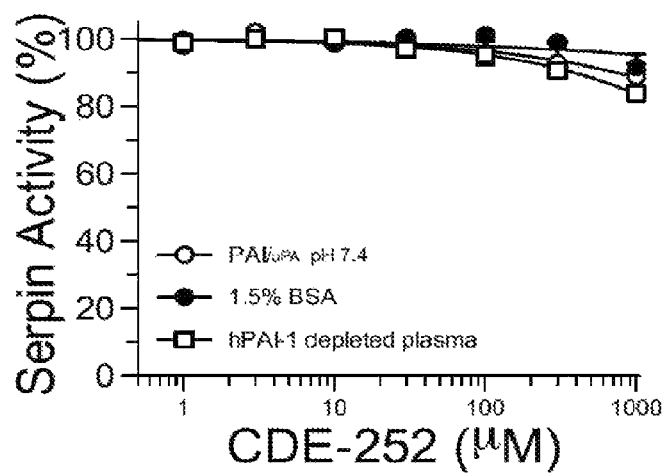
FIG. 2 shows the Serpin activity in the presence of various concentrations of CDE-252.

FIG. 2 is for a compound of structure

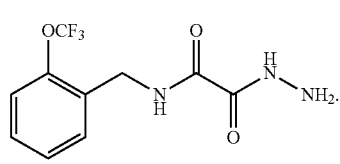

(CDE-252)

Figure 3:
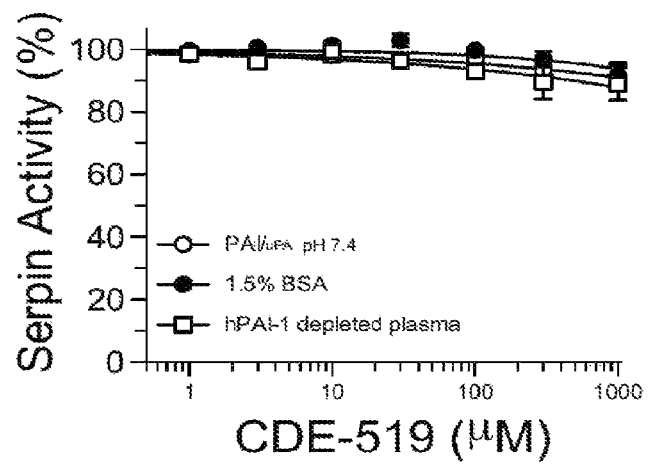
FIG. 3 shows the Serpin activity in the presence of various concentrations of CDE-519.

FIG. 3 is for a compound of structure

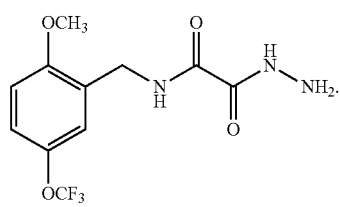

(CDE-519)

Figure 4:
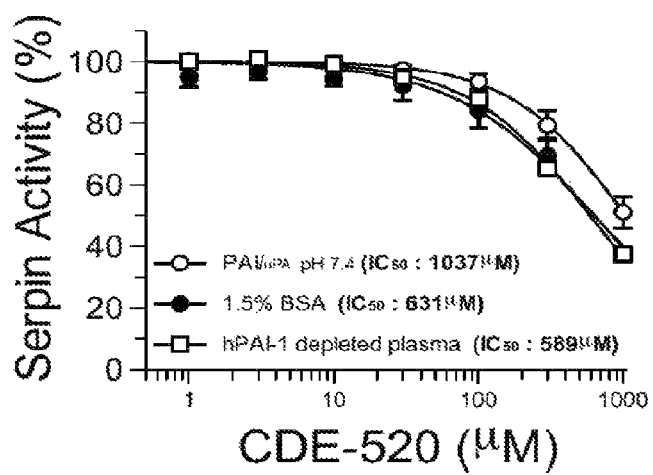
FIG. 4 shows the Serpin activity in the presence of various concentrations of CDE-520.

FIG. 4 is for a compound of structure

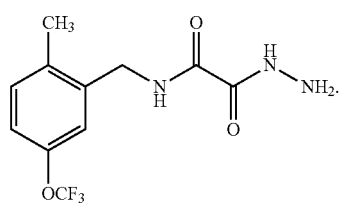

(CDE-520)

Figure 5:
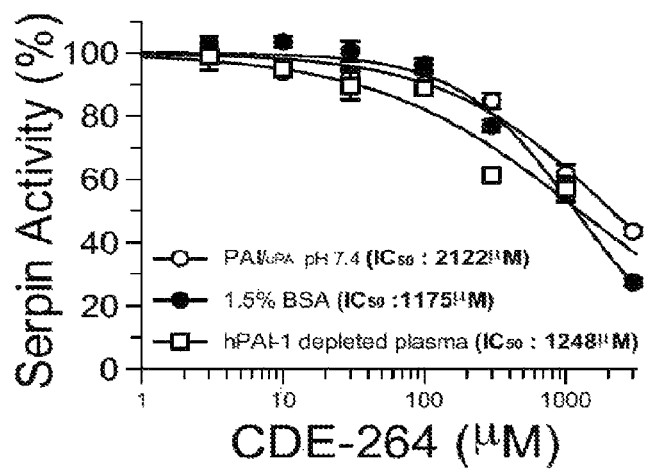
FIG. 5 shows the Serpin activity in the presence of various concentrations of CDE-264.

FIG. 5 is for a compound of structure

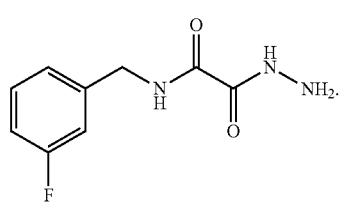

(CDE-264)

Figure 6:
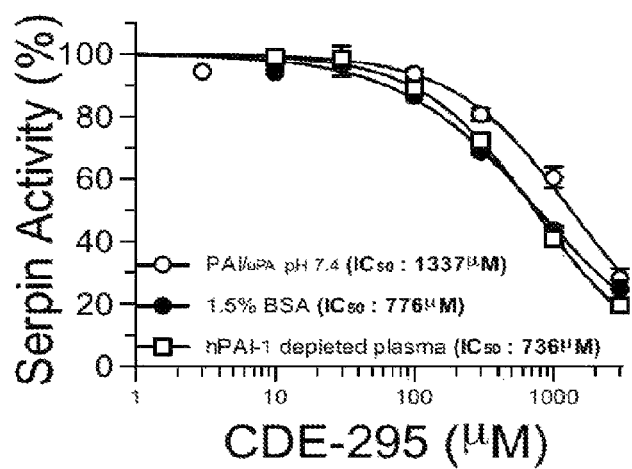
FIG. 6 shows the Serpin activity in the presence of various concentrations of CDE-295.

FIG. 6 is for a compound of structure (CDE-295)
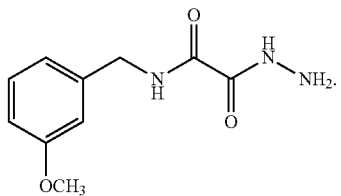

Figure 7:
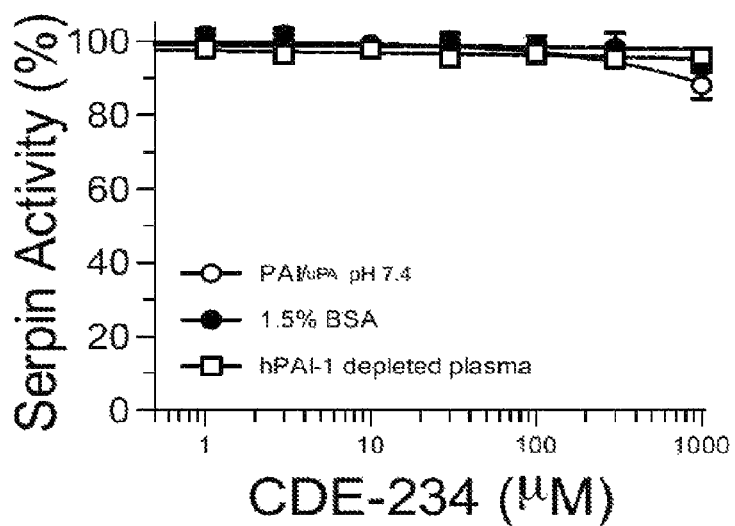
FIG. 7 shows the Serpin activity in the presence of various concentrations of CDE-234.

FIG. 7 is for a compound of structure (CDE-234)
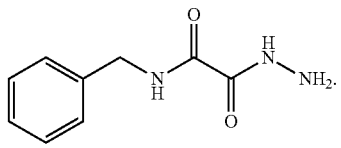

Figure 8:
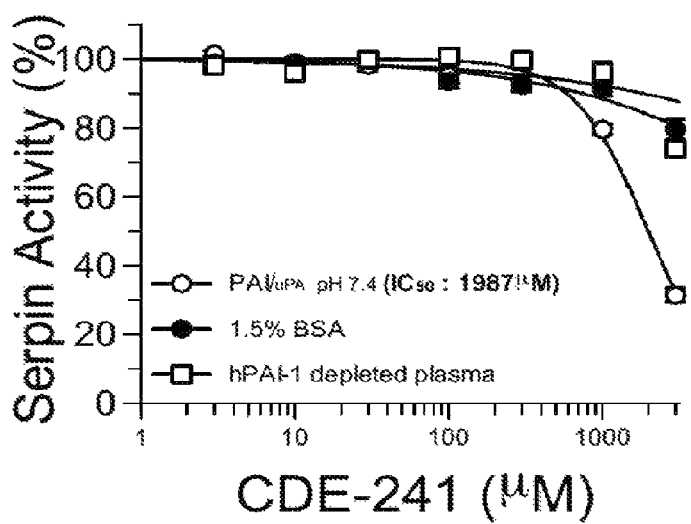
FIG. 8 shows the Serpin activity in the presence of various concentrations of CDE-241.

FIG. 8 is for a compound of structure (CDE-241)
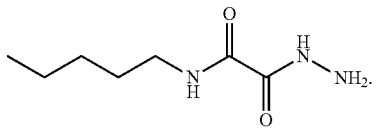

Figure 9:
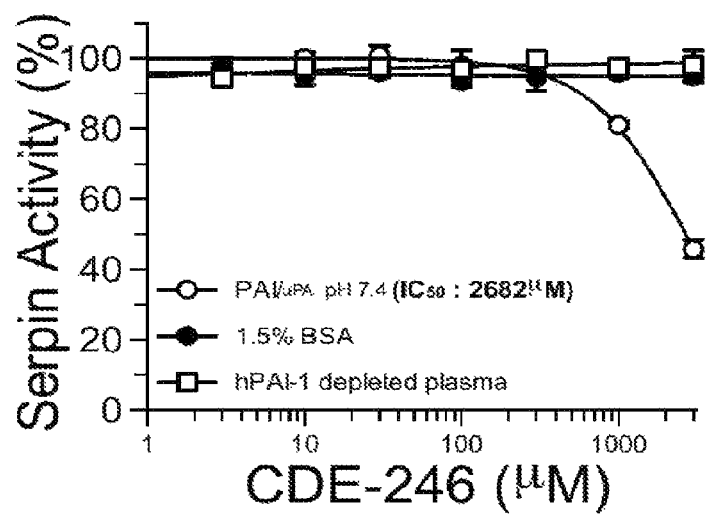
FIG. 9 shows the Serpin activity in the presence of various concentrations of CDE-246.

FIG. 9 is for a compound of structure (CDE-246)
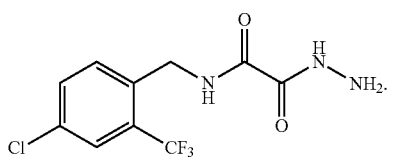

Figure 10:
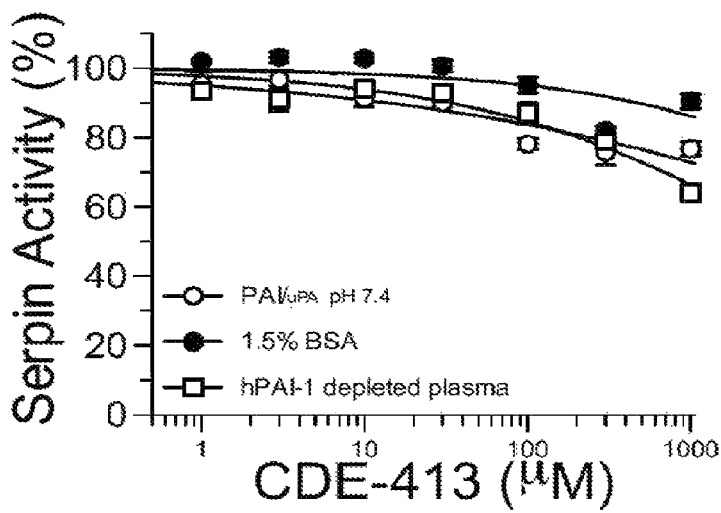
FIG. 10 shows the Serpin activity in the presence of various concentrations of CDE-413.

FIG. 10 is for a compound of structure (CDE-413)
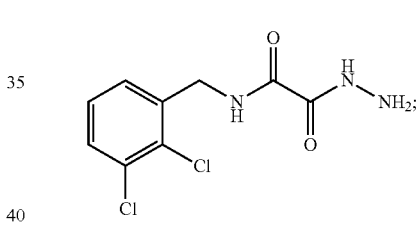

Figure 11:
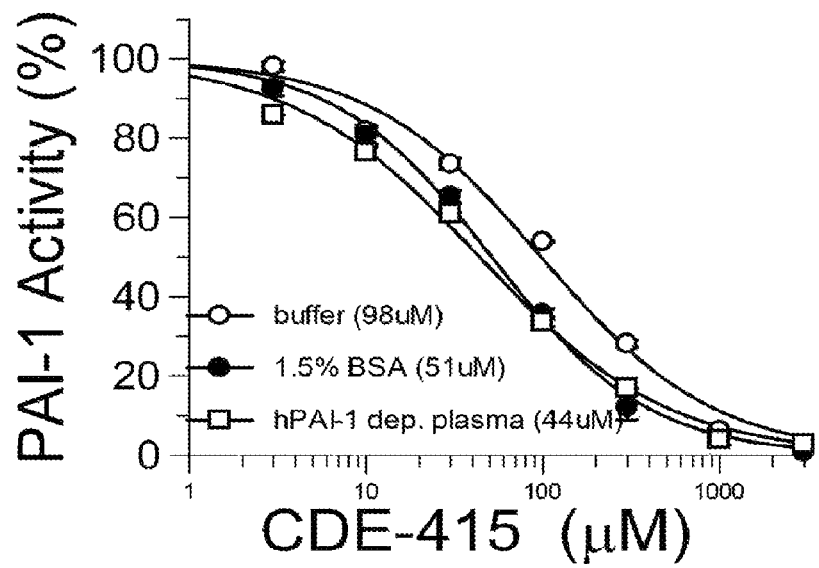
FIG. 11 shows the Serpin activity in the presence of various concentrations of CDE-415.

FIG. 11 is for a compound of structure (CDE-415)
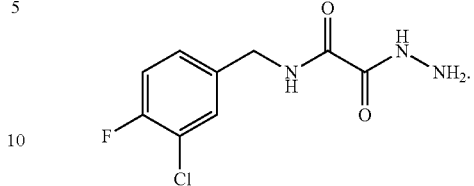

Figure 12:
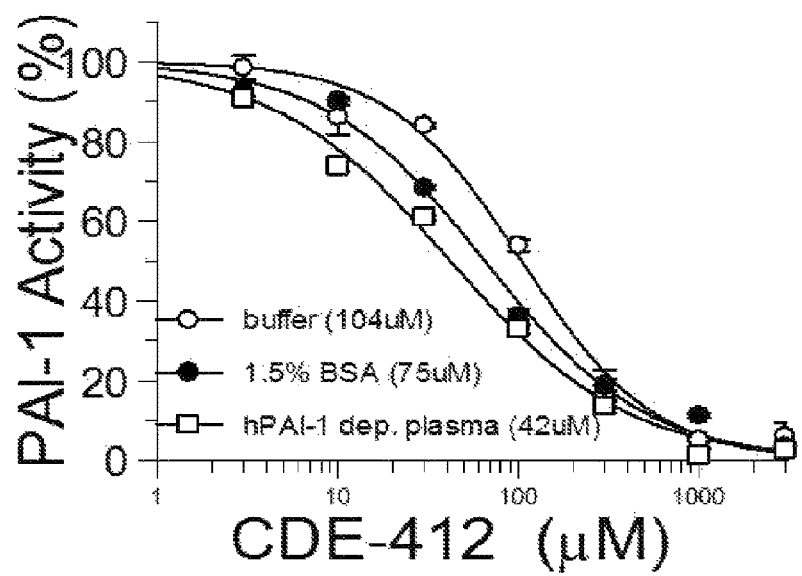
FIG. 12 shows the Serpin activity in the presence of various concentrations of CDE-412.

FIG. 12 is for a compound of structure (CDE-412)
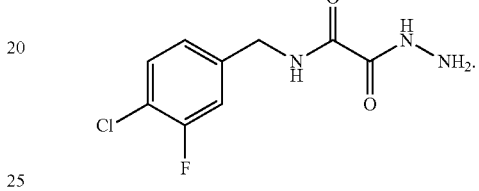

Figure 13:
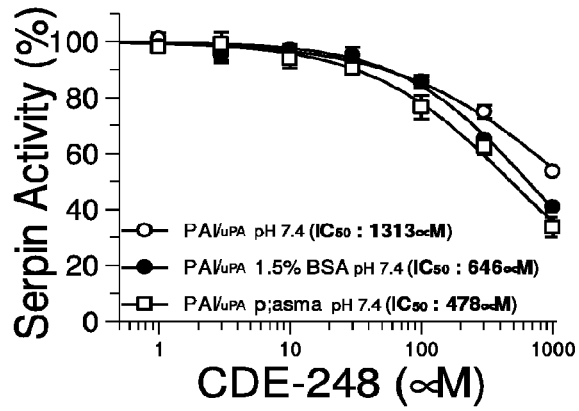
FIG. 13 shows the Serpin activity in the presence of various concentrations of CDE-248.
Figure 13:
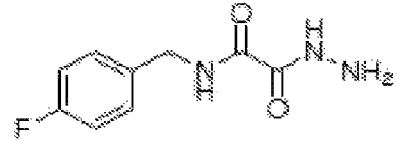
Figure 14:
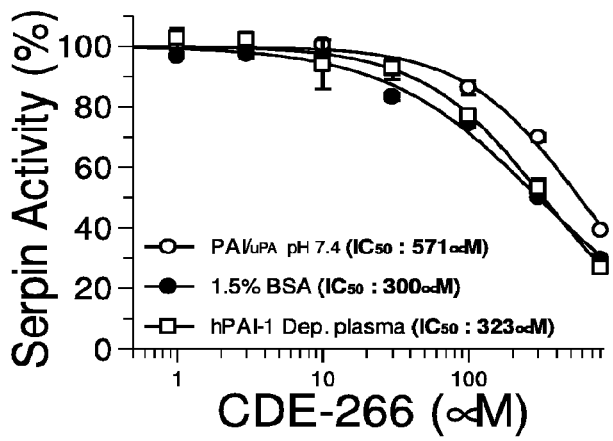
FIG. 14 shows the Serpin activity in the presence of various concentrations of CDE-266.
Figure 14:
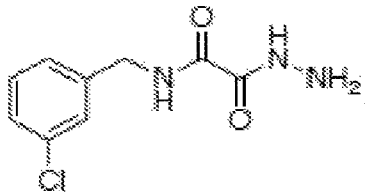
Figure 15:
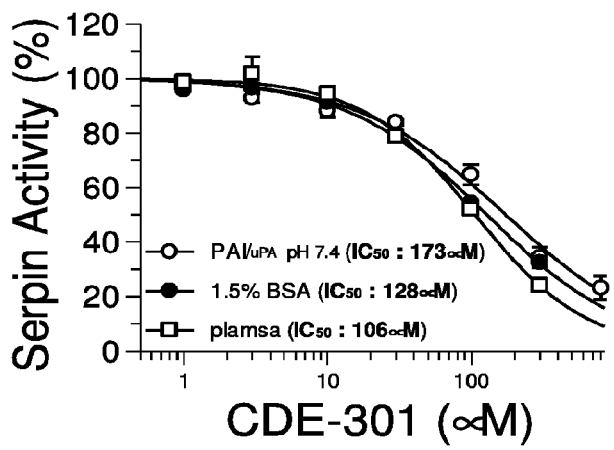
FIG. 15 shows the Serpin activity in the presence of various concentrations of CDE-301.
Figure 15:
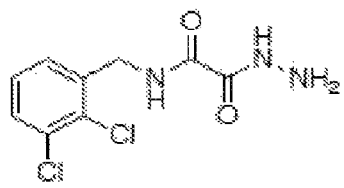

These data compare to those of monohalophenyl compounds CDE-248 and CDE-266 (FIGS. 13 and 14, respectively), as well as to various other dihalophenyl compounds:

(CDE-301, FIG. 15)
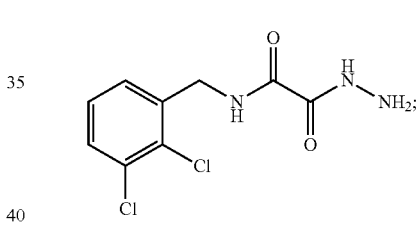

Figure 16:
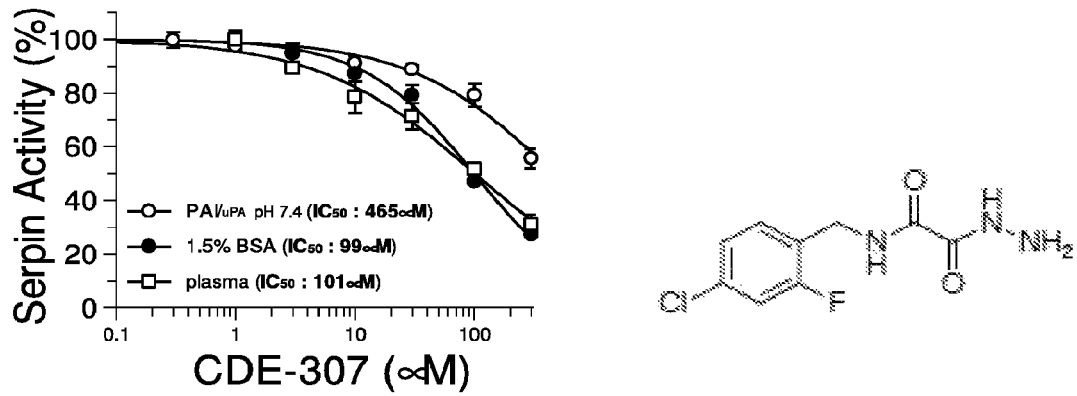
FIG. 16 shows the Serpin activity in the presence of various concentrations of CDE-307.

FIG. 15);

(CDE-307, FIG. 16)
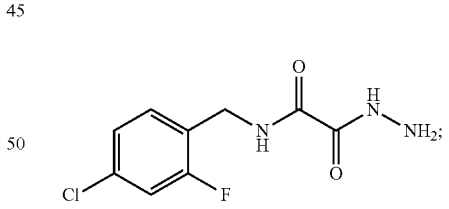

Figure 17:
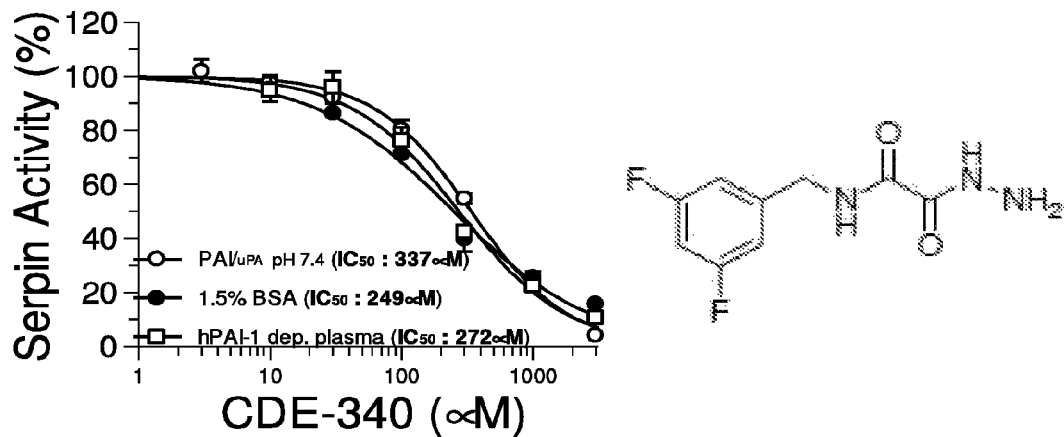
FIG. 17 shows the Serpin activity in the presence of various concentrations of CDE-340.

FIG. 16);

(CDE-340, FIG. 17)
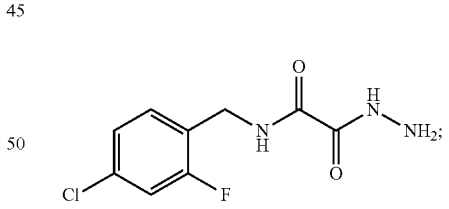

Figure 18:
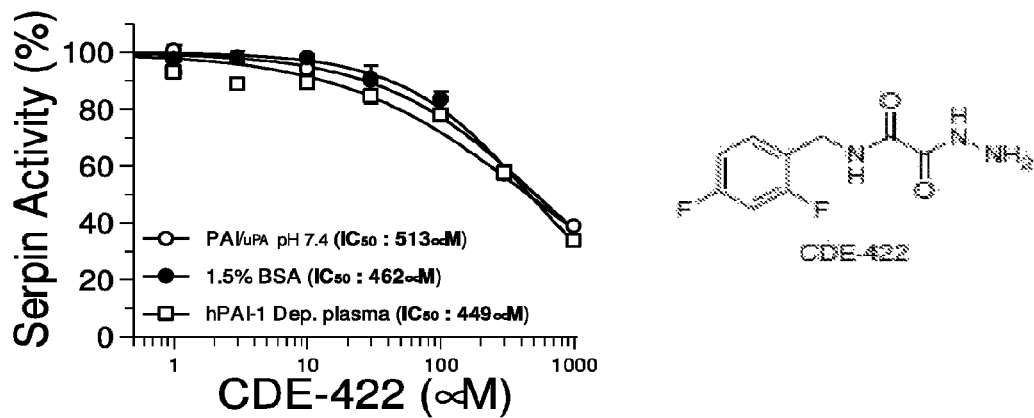
FIG. 18 shows the Serpin activity in the presence of various concentrations of CDE-422.

FIG. 17);

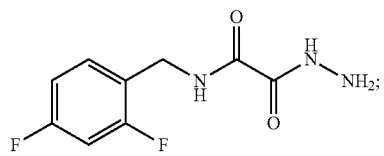
(CDE-422, FIG. 18)

Figure 19:
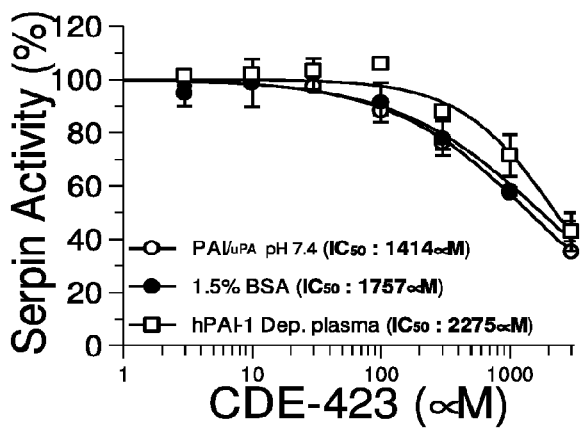
FIG. 19 shows the Serpin activity in the presence of various concentrations of CDE-423.
Figure 19:
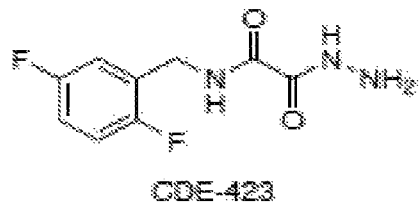

FIG. 18);

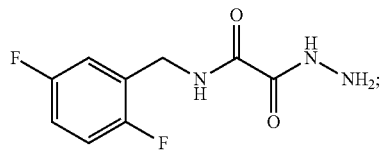
(CDE-423, FIG. 19)

Figure 20:
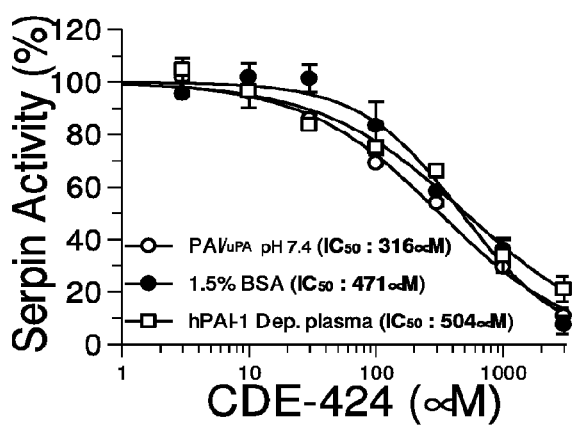
FIG. 20 shows the Serpin activity in the presence of various concentrations of CDE-424.
Figure 20:
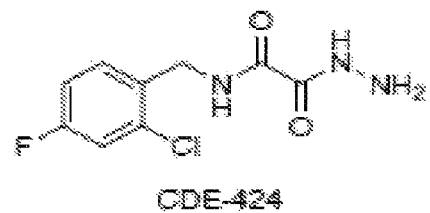

FIG. 19);

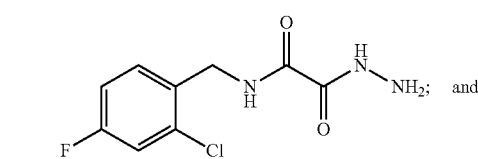
(CDE-424, FIG. 20); and

FIG. 20); and

Figure 21:
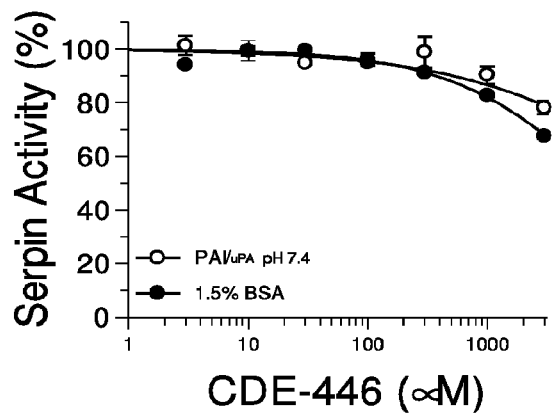
FIG. 21 shows the Serpin activity in the presence of various concentrations of CDE-446.
Figure 21:
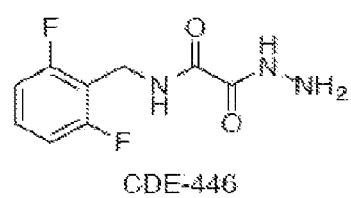

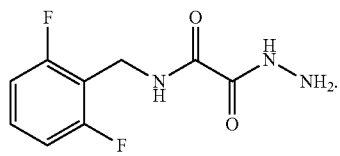
(CDE-446, FIG. 21)

FIG. 21).

What is claimed:

1. A method of inhibiting plasminogen activator inhibitor-1 (PAI-1) comprising contacting PAI-1 with a compound which is

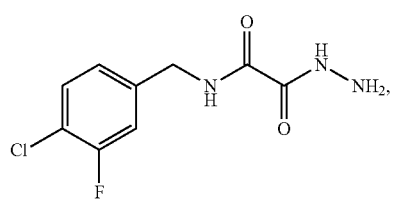

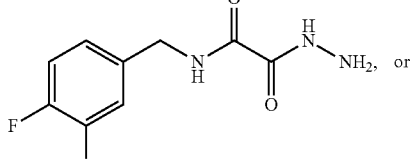 or

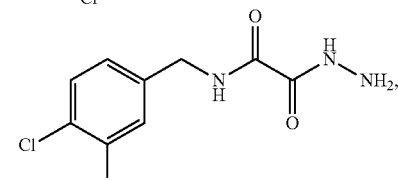

in an amount effective to inhibit PAI-1.

2. A method of treating fibrosis, comprising administering to a subject in need thereof a compound which is

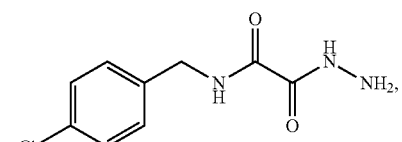

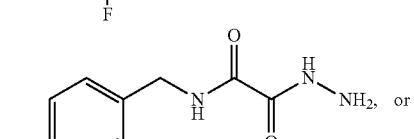 or

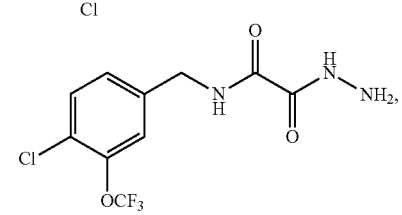

or a pharmaceutically acceptable salt thereof, in an amount effective to treat fibrosis.

3. The method of claim 2, wherein the fibrosis is pulmonary fibrosis, renal fibrosis, cardiac fibrosis, hepatic fibrosis, or scleroderma.

4. The method of claim 1, wherein the compound is

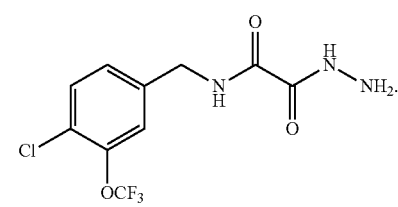 [SMILES: NNC(=O)C(=O)NCc1ccc(Cl)c(OC(F)(F)F)c1]

* * * * *